United States Patent
Lyon et al.

(10) Patent No.: US 8,361,510 B2
(45) Date of Patent: Jan. 29, 2013

(54) NANOGELS FOR CELLULAR DELIVERY OF THERAPEUTICS

(75) Inventors: Louis Andrew Lyon, Marietta, GA (US); John McDonald, Arnoldsville, GA (US); Erin Beth Dickerson, Atlanta, GA (US); William Hobart Blackburn, Mableton, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 110 days.

(21) Appl. No.: 12/997,983

(22) PCT Filed: Jun. 16, 2009

(86) PCT No.: PCT/US2009/047555
§ 371 (c)(1),
(2), (4) Date: Dec. 14, 2010

(87) PCT Pub. No.: WO2010/005741
PCT Pub. Date: Jan. 14, 2010

(65) Prior Publication Data
US 2011/0091562 A1    Apr. 21, 2011

Related U.S. Application Data

(60) Provisional application No. 61/061,715, filed on Jun. 16, 2008.

(51) Int. Cl.
*A61K 9/51* (2006.01)
*A61K 38/04* (2006.01)
*C12N 15/11* (2006.01)
*C07H 21/02* (2006.01)

(52) U.S. Cl. ............ 424/490; 514/44 A; 536/24.5; 530/327

(58) Field of Classification Search .............. None
See application file for complete search history.

(56) References Cited

U.S. PATENT DOCUMENTS

| | | | |
|---|---|---|---|
| 7,056,704 B2* | 6/2006 | Tuschl et al. ............ | 435/91.1 |
| 2003/0064477 A1* | 4/2003 | Band et al. ............. | 435/69.2 |
| 2004/0180823 A1* | 9/2004 | Pasquale et al. ......... | 514/12 |
| 2005/0137334 A1* | 6/2005 | Mondain-Monval et al. .. | 525/71 |
| 2005/0232880 A1* | 10/2005 | Hu et al. ............... | 424/66 |
| 2007/0231360 A1* | 10/2007 | Peyman ................. | 424/422 |

FOREIGN PATENT DOCUMENTS
EP    1852441    11/2007

OTHER PUBLICATIONS

Caplen (Expert Opin. Biol. Ther. 2003, vol. 3, pp. 575-586).*
Check (Nature, 2003, vol. 425, pp. 10-12).*
Cejka et al (Clinical Science 110: 47-58, 2006).*
Pouton et al (Adv. Drug Del. Rev. 46: 187-203, 2001).*
Read et al (Adv. Gen. 53:19-46, 2005).*
Mahato et al. (Expert Opinion on Drug Delivery, Jan. 2005, vol. 2, No. 1, pp. 3-28).*
Nguyen et al (Curr. Opin. Mol. Ther. 10(2): 158-167, 2008).*
Grossman et al (Neuro-Oncology 6: 32-40, 2004).*
Rudin et al (J. Clin. Oncol.26(6): 870-876, Feb. 2008).*
Moulder et al (Clin. Cancer Res. 14(23): 7909-7916, Dec. 2008).*
Sershen et al (Biomed Mater Res, 51, 293-298, 2000).*
Berndt et al (Langmuir 2006, 22, 459-468).*
Nozawa et al (Cancer Sci 2006; 97: 1115-1124).*
Dykxhoorn DM, et al., (Gene Ther (2006) 13(6):541-552).*
Lee, Hyukjin et al., "Target-Specific Intracellular Delivery of siRNA using Degradable Hyaluronic Acid Nanogels", ScienceDirect, Journal of Controlled Release, 2007, pp. 245-252.
Blackburn, William H . et al., "Size Controlled Synthesis of Monodispersed, Core/Shell Nanogels", Colloid and Polymer Science, vol. 286, No. 5, May 2008, pp. 1-18.
Li, Shyh-Dar et al., "Tumor-Targeted Delivery of siRNA by Self-Assembled Nanoparticles", Molecular Therapy, vol. 16, No. 1, Jan. 2008, pp. 163-169.
Kassouf, Wassim et al., Antitumor Effect and Potentiation of Docetaxel Activity in Human Bladder Cancer Cells Treated with Gefitinib ('Iressa', ZD1839), Proc. American Association for Cancer Research, vol. 45, 2004, Abstract #4531.
International Search Report and Written Opinion dated Sep. 15, 2009 issued by the United States Patent and Trademark Office for related PCT Application No. PCT/US2009/047555.

* cited by examiner

*Primary Examiner* — Richard Schnizer
(74) *Attorney, Agent, or Firm* — Troy S. Kleckley; Troutman Sanders LLP

(57) ABSTRACT

The various embodiments of the present disclosure relate generally to nanogels for the cellular delivery of therapeutics and methods of using the same. More particularly, the various embodiments of the present invention are directed to systems and methods for the targeted treatment of neoplastic using nanogel-based technologies. In an embodiment of the present invention, a nanogel-based delivery system comprises: a nanogel comprising a crosslinked polymer particle; and an active agent contained substantially within the nanogel, wherein the active agent is non-covalently associated with the nanogel.

19 Claims, 6 Drawing Sheets

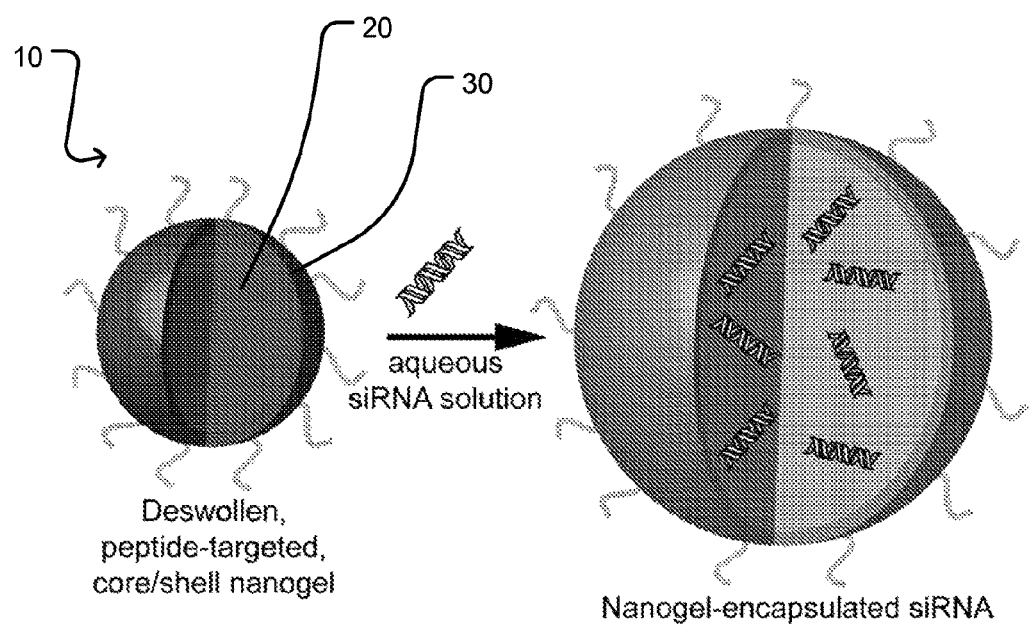
FIGURE 1
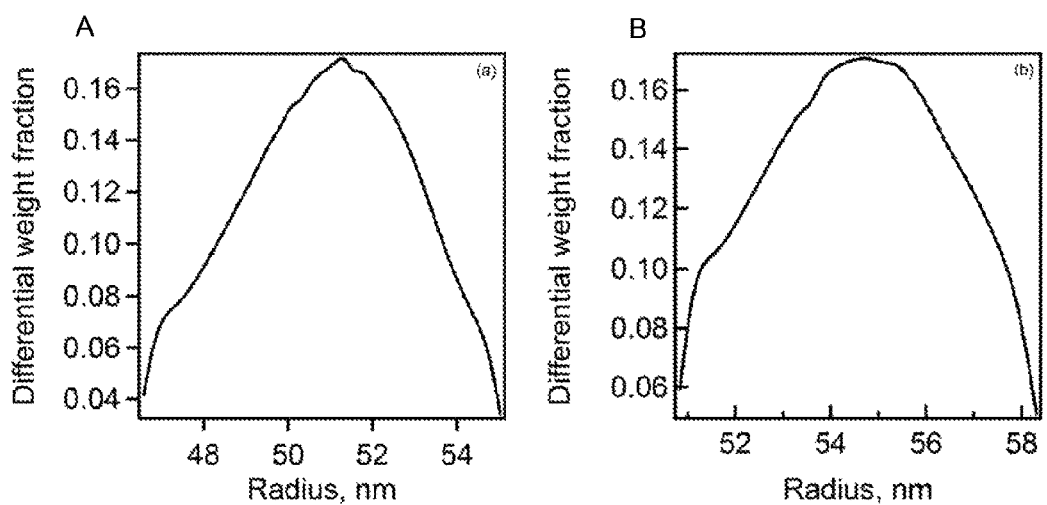
FIGURES 2A-B

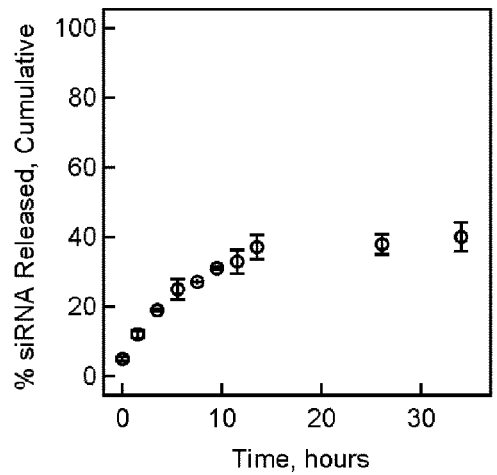
FIGURE 3
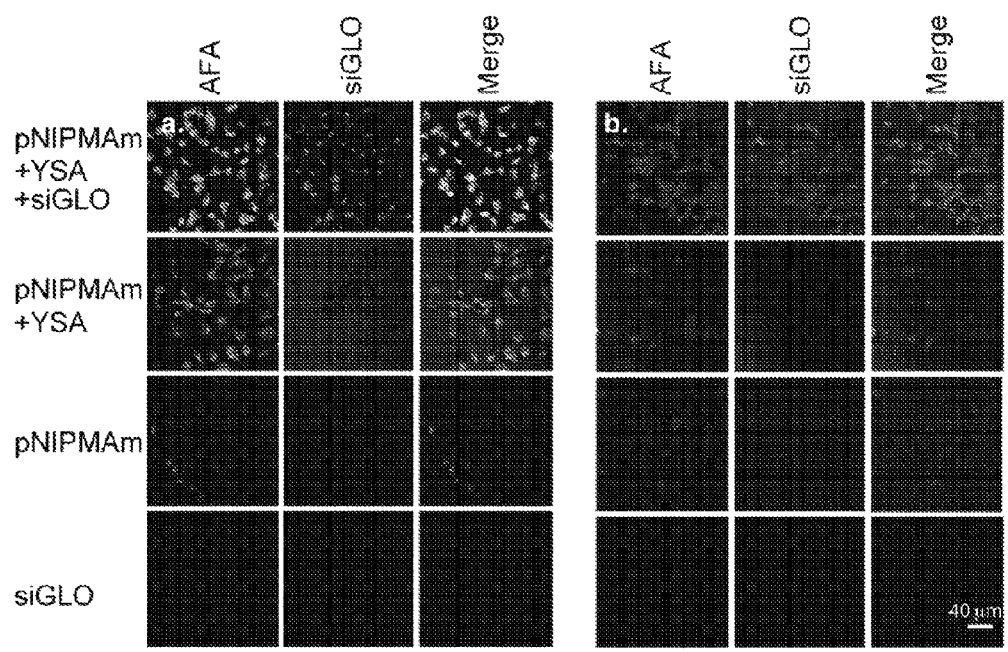
FIGURES 4A-B

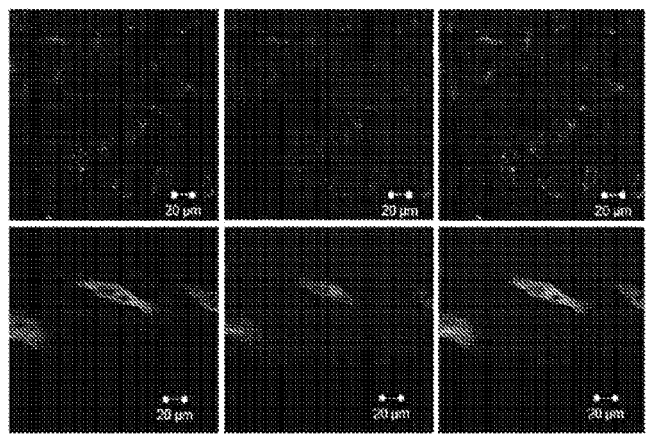
FIGURE 5
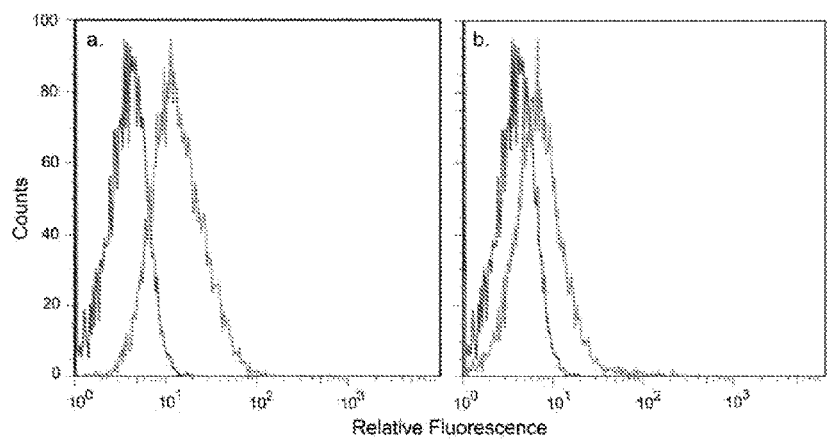
FIGURES 6A-B
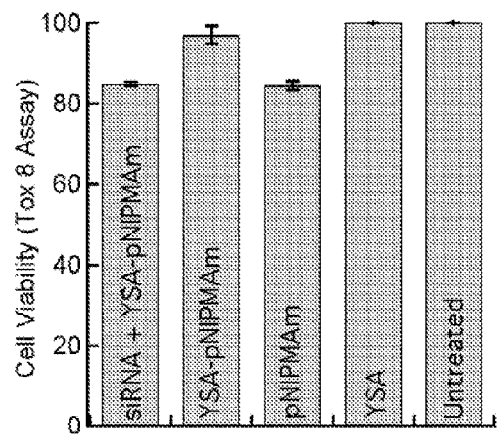
FIGURE 7

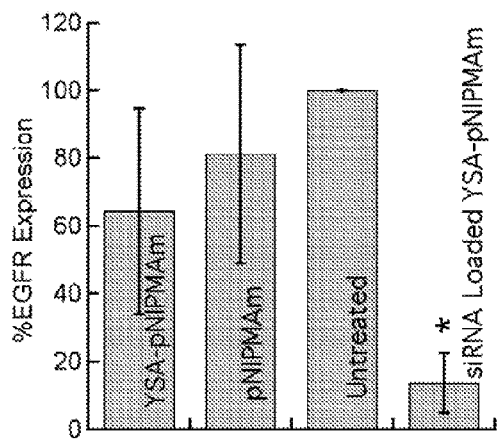
FIGURE 8
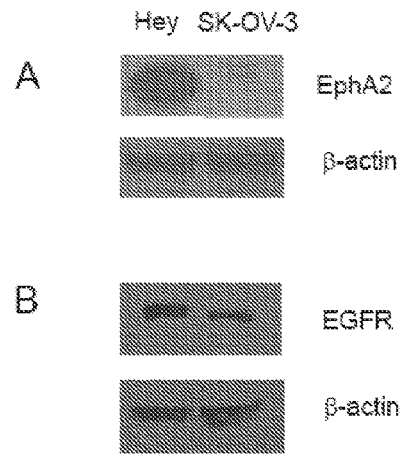
FIGURES 9A-B
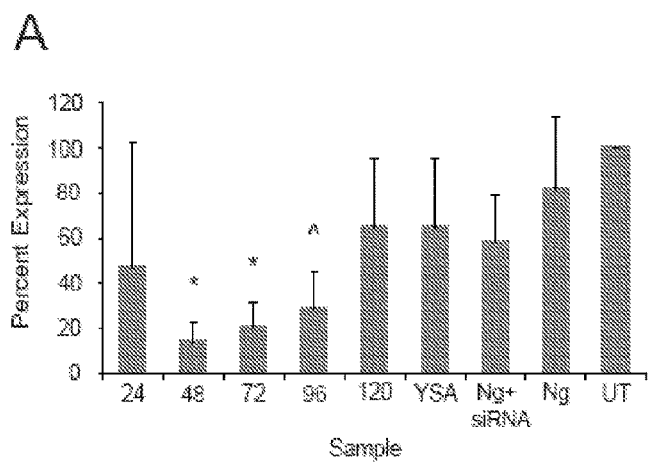
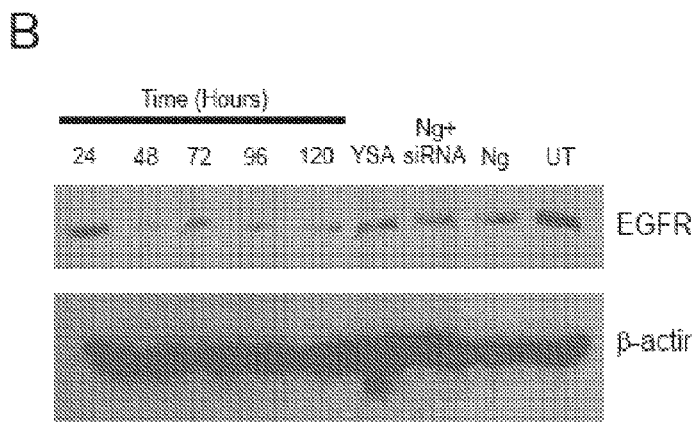
FIGURES 10A-B

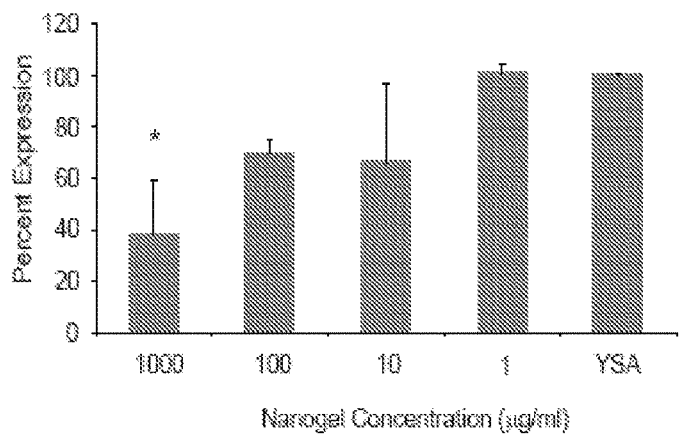
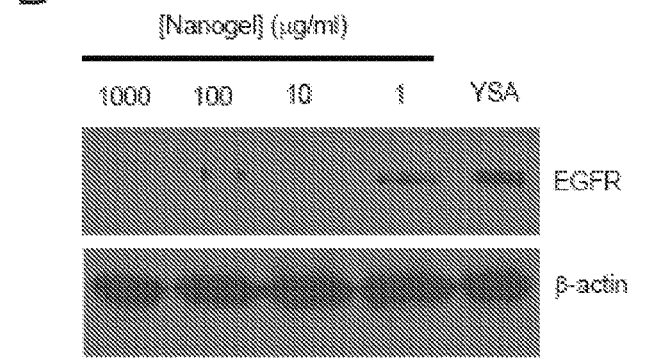
FIGURES 11A-B
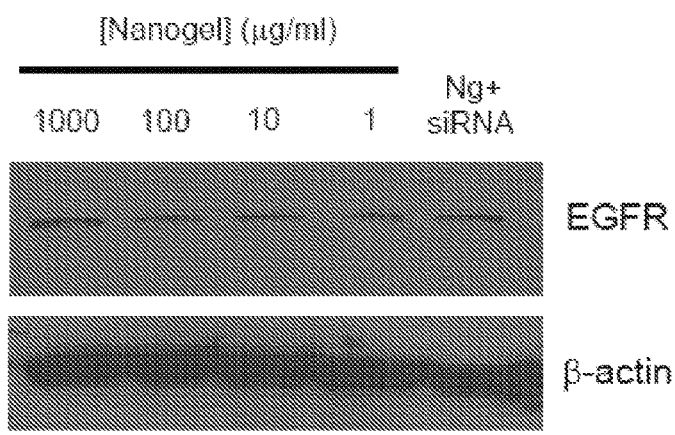
FIGURE 12

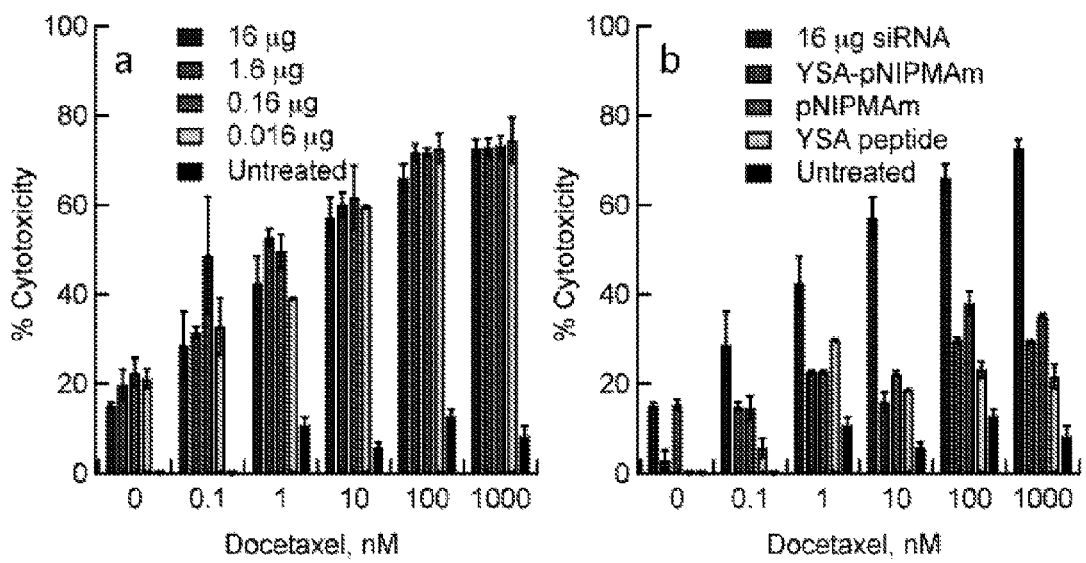
FIGURES 13A-B
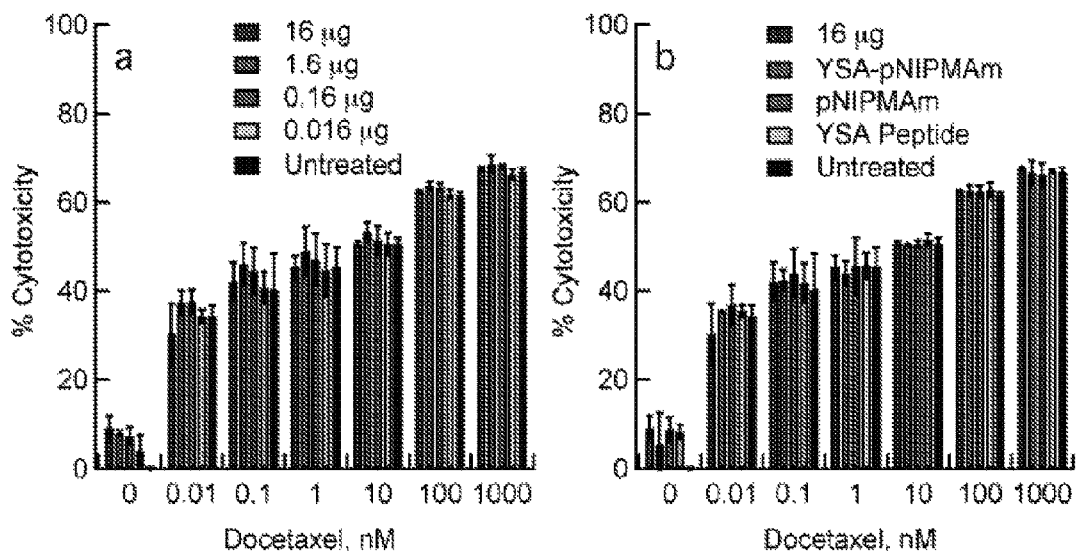
FIGURES 14A-B

NANOGELS FOR CELLULAR DELIVERY OF THERAPEUTICS

CROSS-REFERENCE TO RELATED APPLICATIONS

This application, filed under 35 U.S.C. §371, is a U.S. National Stage Application of International Patent Application Ser. No. PCT/US2009/047555, filed 16 Jun. 2009, entitled Nanogels for Cellualr Delivery of Therapeutics, which claims, under 35 U.S.C. §119(e), the benefit of U.S. Provisional Application Ser. No. 61/061,715, filed 16 Jun. 2008, the entire contents and substance of which are hereby incorporated by reference as if fully set forth below.

STATEMENT REGARDING FEDERALLY SPONSORED RESEARCH

This invention was made with U.S. Government support under Grant No. 1 R21EB 006499-01 awarded by the National Institutes of Health. The U.S. Government has certain Rights in the invention.

TECHNICAL FIELD OF THE INVENTION

The various embodiments of the present disclosure relate generally to nanogels for the cellular delivery of therapeutics and methods of using the same. More particularly, the various embodiments of the present invention are directed to systems and methods for the targeted treatment of neoplastic disease using nanogel-based technologies.

BACKGROUND OF THE INVENTION

Significant effort has been invested in the design of colloidal drug carriers in order to improve drug localization and bioavailability. Ideally, an actively targeted particulate drug carrier will increase the therapeutic efficacy of a drug by delivery to the diseased site, while reducing drug-associated side effects. Attainment of this goal would greatly advance treatment of diseases (e.g., cancer) where the toxic effects of therapeutics administered systemically may outweigh their benefit. To date, many types of delivery vehicles have been explored for in vitro and in vivo drug delivery applications, including inorganic nanoparticles, polyelectrolyte complexes, liposomes, block co-polymer micelles, and polymeric nanoparticles.

A particularly compelling phenomenon from the standpoint of cancer therapy is RNA interference (RNAi). RNAi is a relatively new approach to gene silencing, which has been demonstrated effective both in vitro and in vivo. This technique generally employs small 21-25 nucleotide long double stranded small interfering RNAs (or siRNAs) to inhibit gene expression through degradation of a targeted mRNA. Whereas the potential for therapeutic oncology applications exist where siRNA would be used to specifically shut down genes necessary for tumor growth, the lack of efficient methods for in vivo siRNA delivery prevent widespread therapeutic use. In addition to the confounding issues associated with systemic, intravenous delivery of siRNA, its polyanionic nature and high molecular weight (~13 kDa) prevent transport across the cell membrane. Thus, effective siRNA carriers must enable efficient transport through the vasculature to the tumor, and then must additionally enable intracellular delivery of the cargo.

A common method currently used for siRNA delivery in vitro employs cationic lipid-based carriers or polyelectrolytes. These charged moieties form polyplexes with the siRNA, forming aggregates that can be taken up into the cells, thereby delivering the siRNA to the cytosol. However, these carriers can have notable drawbacks with respect to toxicity and difficulties in specific cell targeting, thereby giving rise to a need for alternative delivery methods. A number of new approaches have been reported that overcome some of the shortcomings of lipid-based approaches. For example, Schiffelers et al. used an RGD (Arg—Gly—Asp peptide ligand)-PEG-PEI complex to target siRNA to tumor neovasculature. (Cancer siRNA therapy by tumor selective delivery with ligand-targeted sterically stabilized nanoparticle. Nucleic Acids Res. 32 (2004)). Song et al. presented the use of a protamine-antibody fusion protein using the Fab fragment of HIV-1 envelope antibody for siRNA delivery. (Antibody mediated in vivo delivery of small interfering RNAs via cell-surface receptors. Nat. Biotechnol. 23, 709-717 (2005)). Another targeting motif has been the use of liposomes in the form of an immunoliposome complex reported by Pirollo et al. (Materializing the Potential of Small Interfering RNA via a Tumor-Targeting Nanodelivery System. Cancer Res. 67, 2938-2943 (2007)). A number of other similar approaches have been taken and these siRNA carriers have enabled certain degrees of success. However, issues of toxicity, leakiness, and payload capacity still persist, especially in the context of in vivo gene silencing.

Accordingly, there is a need for systems and methods for the efficient cellular delivery of therapeutics. It is to the provision of such systems and methods for the efficient cellular delivery of therapeutics using nanogel-based technologies that the various embodiments of the present invention are directed.

BRIEF SUMMARY OF THE INVENTION

Various embodiments of the present invention are directed to nanogels for the cellular delivery of therapeutics and methods of using the same. More particularly, the various embodiments of the present invention are directed to systems and methods for the targeted treatment of neoplastic disease using nanogel-based technologies.

An aspect of the present invention comprises a nanogel-based delivery system comprising: a nanogel comprising a crosslinked polymer particle; and an active agent contained substantially within the nanogel, wherein the active agent is non-covalently associated with the nanogel. In one embodiment of the present invention, the crosslinked polymer particle comprises poly(N-isopropylmethacrylamide) and N,N'-methylenebis(acrylamide). In some embodiments of the present invention, the nanogel further comprises a crosslinked polymer shell comprising a functionalization agent, wherein the crosslinked polymer shell is disposed substantially around the crosslinked polymer particle. IN such embodiments, the crosslinked polymer shell can comprise poly(N-isopropylmethacrylamide), N,N'-methylenebis (acrylamide), and aminopropylmethacryamide.

In an embodiment of the present invention, the active agent is a small interfering ribonucleic acid (siRNA). More specifically, the siRNA can comprise substantial sequence identity to a target gene relevant to neoplastic disease.

In an embodiment of the present invention, the nanogel can further comprise a targeting moiety, wherein the targeting moiety is attached to the crosslinked polymer shell through the functionalization agent, and wherein the targeting moiety is displayed on at least a portion of the crosslinked polymer shell. In such an embodiment, the targeting moiety can comprise a peptide having the amino acid sequence YSAYPDS- VPMMSC (SEQ ID NO 1). In one embodiment of the present invention, the active agent can comprise a siRNA having substantial sequence identity to a gene encoding epidermal growth factor receptor.

An aspect of the present invention comprises a method of delivering an active agent into a cell, the method comprising: contacting a nanogel with a cell, the nanogel comprising a crosslinked polymer particle, and an active agent contained substantially within the nanogel, wherein the active agent is non-covalently associated with the nanogel; and delivering an active agent to the cell. In one embodiment of the present invention, the active agent comprises a siRNA. In an embodiments of the present invention, the crosslinked polymer particle comprises poly(N-isopropylmethacrylamide) and N,N'-methylenebis(acrylamide).

In some embodiments of the present invention, the nanogel further comprises a targeting moiety and crosslinked polymer shell comprising a functionalization agent, the crosslinked polymer shell disposed substantially around the crosslinked polymer particle, wherein the targeting moiety is attached to the crosslinked polymer shell through the functionalization agent, and wherein the targeting moiety is displayed on at least a portion of the crosslinked polymer shell. In one embodiment, the crosslinked polymer shell comprises poly (N-isopropylmethacrylamide), N,N'-methylenebis(acrylamide), and aminopropylmethacryamide.

A method of delivering an active agent into a cell can further comprise reducing expression of a target gene, wherein the siRNA has substantial sequence identity to the target gene. In one embodiment of the present invention, the target gene encodes one or more of an anti-apoptotic molecule, a growth factor, a growth factor receptor, a mitotic spindle protein, a cell cycle protein, an angiogenic factor, an oncogene, an intracellular signal transducer, or a molecular chaperone. In an exemplary embodiment of the present invention, the targeting moiety comprises a peptide having the amino acid sequence YSAYPDSVPMMSC (SEQ ID NO 1), and wherein the active agent is a siRNA having substantial sequence identity to the target gene, the target gene encoding epidermal growth factor receptor.

Another aspect of the present invention comprises a method for treating neoplastic disease comprising: administering to a subject having neoplastic disease an effective amount of a nanogel comprising a crosslinked polymer particle; a crosslinked polymer shell comprising a functionalization agent, wherein the crosslinked polymer shell is disposed substantially around the crosslinked polymer particle; a targeting moiety, wherein the targeting moiety is attached to the crosslinked polymer shell through the functionalization agent, and wherein the targeting moiety is displayed on at least a portion of the crosslinked polymer shell; and an active agent contained substantially within the nanogel, wherein the active agent is non-covalently associated with the nanogel.

In one embodiment of the present invention, the crosslinked polymer particle comprises poly(N-isopropylmethacrylamide) and N,N'-methylenebis(acrylamide). In one embodiment of the present invention, the crosslinked polymer shell comprises poly(N-isopropylmethacrylamide), N,N'-methylenebis(acrylamide), and aminopropylmethacryamide. In one embodiment of the present invention, the active agent is a siRNA.

According to the various embodiments of the present invention, a method for treating neoplastic disease can further comprise reducing expression of a target gene, wherein the siRNA has substantial sequence identity to the target gene. In such embodiments of the present invention, the target gene encodes one or more of an anti-apoptotic molecule, a growth factor, a growth factor receptor, a mitotic spindle protein, a cell cycle protein, an angiogenic factor, an oncogene, an intracellular signal transducer, or a molecular chaperone. More specifically, in an embodiment of the present invention, the targeting moiety comprises a peptide having the amino acid sequence YSAYPDSVPMMSC (SEQ ID NO 1), and wherein the target gene encodes epidermal growth factor receptor.

In some embodiments of the present invention, a method for treating neoplastic disease can further comprise increasing sensitivity of the subject to a chemotherapeutic agent. In such embodiments, the chemotherapeutic agent can comprise paclitaxel or docetaxel.

Other aspects and features of embodiments of the present invention will become apparent to those of ordinary skill in the art, upon reviewing the following description of specific, exemplary embodiments of the present invention in conjunction with the accompanying figures.

BRIEF DESCRIPTION OF DRAWINGS

FIG. 1 schematically illustrates the non-covalent encapsulation of siRNA in peptide-targeted core/shell nanogels.

FIGS. 2A and B graphically depict the differential weight fraction plots for (A) pNIPMAm core nanogels and (B) pNIPMAm core/shell nanogels, as determined by AFFF-MALLS.

FIG. 3 graphically illustrates the siRNA release profile from nanogels at 37° C. in PBS containing 10% fetal bovine serum. The error bars represent ±one standard deviation about the mean value (n=3).

FIGS. 4A and B provide confocal microscopy images of (A) Hey cells and (B) BG-1 cells following exposure to siGLO-loaded/YSA-conjugated pNIPAMAm nanogels, YSA-nanogels alone, unlabeled nanogels, and siGLO alone.

FIG. 5 provides confocal microscopy images of Hey cells (top) following exposure to siGLO-loaded/YSA-conjugated nanogels after 1 h ephrin incubation, and (bottom) following exposure to siGLO-loaded/YSA-conjugated nanogels alone.

FIGS. 6A and B show flow cytometry data comparing (A) cell autofluorescence (first peak) vs. cells incubated with YSA-pNIPMAm nanogels (second peak) and (B) cell autofluorescence (first peak) vs. cells incubated with SCR-pNIPMAm nanogels (second peak).

FIG. 7 demonstrates cell viability as determined with a Tox 8 assay for untreated Hey cells and Hey cells following a four h incubation with EGFR siRNA-loaded YSA-labeled nanogels, YSA-labeled pNIPMAm nanogels, unlabeled pNIPMAm, or YSA peptide alone. Error bars represent ±one standard deviation about the average value (n=3).

FIG. 8 demonstrates EGFR expression, as determined by immunoblot, in Hey cells following a four hour incubation with either unloaded YSA-nanogels, unloaded non-targeted nanogels, or siRNA loaded YSA-nanogels. Error bars represent ±one standard deviation about the average value (n=3, *p<0.01 relative to untreated sample).

FIGS. 9A and B demonstrate expression of (A) EphA2 and (B) EGFR in Hey and SK-OV-3 ovarian cancer cell lines.

FIGS. 10A and B illustrate down-regulation of EGFR by siRNA-loaded nanogels.

FIGS. 11A and B illustrate down-regulation of EGFR by different concentrations of siRNA-loaded nanogels.

FIG. 12 shows the Level of EGFR in SK-OV-3 cells after treatment with siRNA-loaded nanogels.

FIGS. 13A and B demonstrate chemosensitization of Hey cells to docetaxel after exposure to YSA-targeted, siRNA loaded nanogels.

FIGS. 14A and B show the effects of increasing concentrations of docetaxel on SK-OV-3 cells treated with siRNA-loaded nanogels.

DETAILED DESCRIPTION OF THE INVENTION

An aspect of the present invention comprises a nanogel-based delivery system comprising: a nanogel comprising a crosslinked polymer particle; and an active agent contained substantially within the nanogel, wherein the active agent is non-covalently associated with the nanogel.

As used herein, the term "nanogel" refers to a crosslinked polymer particle capable of absorbing a fluid and retaining at least a portion of the fluid to form a swollen crosslinked polymer particle. A nanogel can have many sizes, and these sizes are indicative of the nanogel in solvent swollen form. A nanogel can have an average longest cross-sectional dimension of about 10 nanometers (nm) to about 5 micrometers (μm). In some embodiments of the present invention, a nanogel can have an average longest cross-sectional dimension about 20 nm to about 1 μm. In one embodiment of the present invention, a nanogel may have an average longest cross-sectional dimension of about 20 nm to about 200 nm. In an exemplary embodiment of the present invention, a nanogel may have an average longest cross-sectional dimension of about 50 nm to about 100 nm.

A crosslinked polymer particle can comprise a polymer and a crosslinker. A crosslinked polymer particle can comprise many suitable hydrophilic, hydrophobic, and amphiphilic polymers known in the art. In some embodiment of the present invention, a crosslinked polymer particle can comprise a hydrophilic polymer, including, but not limited to, acrylates, acrylamides, acetates, acrylic acids, vinyl alcohols, glycols, polysaccharides, co-polymers thereof, or combinations thereof. In various embodiments of the present invention, the polymer can have many topologies including, but not limited to, a branched topology, a graft topology, a comb topology, a star topology, a cyclic topology, a network topology, or combinations thereof, among others. The crosslinker of the polymer particles can be many suitable crosslinkers known in the art including, but not limited to, N,N',methylenebis(acrylamide), poly(ethylene glycol) (PEG) diacrylate, N,N'-dihydroxyethylene-bisacrylamide, N,O-(dimethacryloyl)hydroxylamine, ethylene glycol dimethacrylate, divinylbenzene, or combinations thereof.

In an exemplary embodiment of the present invention, a crosslinked polymer particle comprises poly(N-isopropylmethacrylamide) (pNIPMAm) and N,N'-methylenebis(acrylamide) (BIS). In such embodiments, pNIPMAm can comprise about 90% to about 99.9% of the crosslinked polymer particle. Accordingly, BIS can comprise about 10% to about 0.1% of the crosslinked polymer particle.

Nanogels of the present invention are configured to substantially contain an active agent. One of ordinary skill in the art would realize that the composition and crosslink density of the crosslinked polymer particle can be varied based upon the characteristics of the active agent (e.g., size, charge, etc.). One of ordinary skill in the art would realize that the crosslink density (also referred to a mesh size) of the polymer particle may be varied by increasing the crosslinker concentration, decreasing the crosslinker length, or increasing the number of reactive sites on the crosslinker. Similarly, one of ordinary skill in the art would realize that the hydrophobicity of the polymer particle can be varied to accommodate active agents having various solubilities.

In some embodiments of the present invention, the nanogel comprises a core-shell topology, as shown in FIG. 1. In such embodiments, the nanogel 10 comprises a core 20 comprising the crosslinked polymer particle. As such, the terms "crosslinked polymer particle" and "core" may be used interchangeably throughout this disclosure. The nanogel can further comprise a crosslinked polymer shell 30, wherein the shell is disposed substantially around the crosslinked polymer particle.

The shell can have an average thickness of about 5 nanometers to about 300 nanometers in a solvent swollen state. In an exemplary embodiment of the present invention, a shell can have a thickness of about 10 nanometers to about 20 nanometers. In some embodiments of the present invention, the shell may comprise the same polymeric material as the crosslinked polymer particle; however, in some embodiments of the present invention, the shell may comprise a different polymeric material than that of the crosslinked polymer particle. Further, the shell and crosslinked polymer particle may have similar or different crosslink densities and hydrophobicities.

The shell can comprise many suitable hydrophilic, hydrophobic, and amphiphilic polymers known in the art. In some embodiments of the present invention, the shell can comprise a hydrophilic polymer, including, but not limited to, acrylates, acrylamides, acetates, acrylic acids, vinyl alcohols, glycols, polysaccharides, co-polymers thereof, or combinations thereof. The crosslinker of the shell can be many suitable crosslinkers known in the art including, but not limited to, N,N', methylenebis(acrylamide), poly(ethylene glycol) (PEG) diacrylate, N,N'-dihydroxyethylene-bisacrylamide, N,O-(dimethacryloyl)hydroxylamine, ethylene glycol dimethacrylate, divinylbenzene, or combinations thereof.

The shell may further comprise a functionalization agent. A functionalization agent permits surface modification of the nanogel. A functionalization agent can comprise a chemoligation motif. In an embodiment of the present invention, the chemoligation motif can be present at a concentration of about 0.5% to about 15%. A chemoligation motif can include, but is not limited to, an amine, a carboxyl group, an aldehyde, a hydrazide, a sulfhydryl, a hydroxyl, or a ketone. These chemoligation motifs can be used to perform 'click' chemistry (e.g., a Cu(I) catalyzed 3+2 dipolar cycloaddition) a Schiff base transformation, and combinations thereof, which permit surface modification of the nanogel. In embodiments of the present invention, the functionalization agent can comprise N-(2-hydroxypropyl) methacrylamide (HPMA), aminopropylmethacryamide (APMA), aminoethylacrylate, among others. In an exemplary embodiment of the present invention, the functionalization agent is aminopropylmethacryamide.

In an exemplary embodiment of the present invention, a shell comprises poly(N-isopropylmethacrylamide) (pNIPMAm), N,N'-methylenebis(acrylamide) (BIS), and aminopropylmethacryamide (APMA). In such embodiments, pNIPMAm can comprise about 75% to about 99.9% of the shell, BIS can comprise about 10% to about 0.1% of the shell, and APMA can comprise about 0.5% to about 15% of the shell. In an exemplary embodiment of the present invention, the shell comprises 97.5% NIPMAm, 2% BIS, and 0.5% APMA.

A nanogel-based delivery system comprises an active agent contained substantially within the nanogel, wherein the active agent is non-covalently associated with the nanogel. As used herein, the term "active agent" can refer to one or more active agents or components, such as pharmacological component, a therapeutic component, a diagnostic component, a drug component, a biological component or the like. Thus, the terms "active agent," "drug," "therapeutic," "diagnostic," "pharmaceutical," and the like may be used interchangeably throughout this disclosure. An active agent may also comprise one or more pharmaceutical additives including, but not limited to, solubilizers, emulsifiers, buffers, preservatives, carriers, suspending agents, thickening agents, stabilizers, inert components, and the like.

As used herein, the term "active agent" can include, without limitation, a biological or chemical compound such as a simple or complex organic or inorganic molecule, peptide, peptide mimetic, protein (e.g. antibody, growth factor), an antigen or immunogen, small interfering RNA (siRNA), or a polynucleotide, a virus, or a therapeutic agent. Organic or inorganic molecules can include, but are not limited to, a homogenous or heterogeneous mixture of compounds, including pharmaceuticals, radioisotopes, crude or purified plant extracts, and/or an entity that alters, inhibits, activates, or otherwise affects biological or biochemical events, including classes of molecules (e.g., proteins, amino acids, peptides, polynucleotides, nucleotides, carbohydrates, sugars, lipids, nucleoproteins, glycoproteins, lipoproteins, steroids, growth factors, chemoattractants, cytokines, chemokines, etc.) that are commonly found in cells and tissues, whether the molecules themselves are naturally-occurring or artificially created (e.g., by synthetic or recombinant methods).

Examples of such agents include, but are not limited to, agents for gene therapy; analgesics; anti-arthritics; anti-asthmatic agents; anti-cancer agents; anti-cholinergics; anti-convulsants; anti-depressants; anti-diabetic agents; anesthetics; antibiotics; antigens; anti-histamines; anti-infectives; anti-inflammatory agents; anti-microbial agents; anti-fungal agents, anti-Parkinson agents; anti-spasmodics; anti-pruritics; anti-psychotics; anti-pyretics; anti-viral agents; nucleic acids; DNA; RNA; siRNA; polynucleotides; nucleosides; nucleotides; amino acids; peptides; proteins; carbohydrates; lectins; lipids; fats; fatty acids; viruses; immunogens; antibodies and fragments thereof; sera; immunostimulants; immunosuprressants; cardiovascular agents; channel blockers (e.g., potassium channel blockers, calcium channel blockers, beta-blockers, alpha-blockers); anti-arrhythmics; anti-hypertensives; inhibitors of DNA, RNA, or protein synthesis; neurotoxins; vasodilating agents; vasoconstricting agents; gases, growth factors; growth inhibitors; hormones; steroids; steroidal and non-steroidal anti-inflammatory agents; corticosteroids; angiogenic agents; anti-angiogenic agents; hypnotics; muscle relaxants; muscle contractants; sedatives; tranquilizers; ionized and non-ionized active agents; metals; small molecules; pharmaceuticals; hemotherapeutic agents; wound healing agents; indicators of change in the bio-environment; enzymes; enzyme inhibitors; nutrients; vitamins; minerals; coagulation factors; anticoagulants; anti-thrombotic agents; neurochemicals (e.g., neurotransmitters); cellular receptors; radioactive materials; contrast agents (e.g., fluorescence, magnetic, radioactive); nanoparticles (e.g., magnetic, semiconductor, dielectric, or metal); vaccines; modulators of cell growth; modulators of cell adhesion; cell response modifiers; cells; chemical or biological materials or compounds that induce a desired biological or pharmacological effect; and combinations thereof.

In an exemplary embodiment of the present invention, the active agent is a small interfering RNA (siRNA). As used herein, the terms "small interfering RNA," "siRNA," "interfering RNA" or "RNAi" or "interfering RNA sequence" refers to double-stranded RNA (i.e., duplex RNA) that targets (i.e., silences, reduces, or inhibits) expression of a target gene (i.e., by mediating the degradation of mRNAs which are complementary to the sequence of the interfering RNA) when the interfering RNA is in the same cell as the target gene. siRNA thus refers to the double stranded RNA formed by two complementary strands or by a single, self-complementary strand (e.g., a hairpin). Interfering RNA typically has substantial or complete identity to the target gene. The sequence of the siRNA can correspond to the full length target gene, or a sub-sequence (i.e., a portion) thereof. siRNA includes interfering RNA of about 15 to about 60 nucleotides, about 15 to about 50 nucleotides, or about 15 to about 40 nucleotides in length, more typically about 15 to about 30 nucleotides, 15 to about 25 nucleotides, or 19 to about 25 nucleotides, and is preferably about 21 to about 25 nucleotides, about 20 to about 24 nucleotides, about 21 to about 22 nucleotides, or about 21 to about 23 nucleotides. siRNA duplexes may comprise 3' overhangs of about 1 to about 4 nucleotides, preferably of about 2 to about 3 nucleotides, and 5' phosphate termini. The siRNA can be chemically synthesized or may be encoded by a plasmid (e.g., transcribed as sequences that automatically fold into duplexes with hairpin loops). siRNA can also be generated by cleavage of longer dsRNA (e.g., dsRNA greater than about 25 nucleotides in length) with the *E. coli* RNase III or Dicer. These enzymes process the dsRNA into biologically active siRNA. Preferably, dsRNA are at least 50 nucleotides to about 100, 200, 300, 400, or 500 nucleotides in length. A dsRNA may be as long as 1000, 1500, 2000, 5000 nucleotides in length, or longer. The dsRNA can encode for an entire gene transcript or a partial gene transcript.

The siRNA of the present invention can comprise RNA having substantial or complete identity to the target genes involved many diseases. In an exemplary embodiment of the present invention, the siRNA can comprise RNA having substantial or complete identity to a target gene relevant to neoplastic disease (i.e., cancer), including but not limited to, an anti-apoptotic molecule, a growth factor, a growth factor receptor, a mitotic spindle protein, a cell cycle protein, an angiogenic factor, an oncogene, an intracellular signal transducer, a molecular chaperone, and combinations thereof. The term "neoplastic disease" is intended to refer to hyperplasia, tumors, tumorigenesis, cancer, metastasis, cells that have uncontrolled growth, and the like. A person of ordinary skill in the art would realize that gene expression analysis and proteomic analysis of neoplastic cells may prove useful in the identification of suitable target genes.

As used herein, the term "substantial identity" of polynucleotide sequences means that a polynucleotide includes a sequence that has at least 51%, 52%, 53%, 54%, 55%, 56%, 57%, 58%, 59%, 60%, 61%, 62%, 63%, 64%, 65%, 66%, 67%, 68%, or 69%, 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence.

In an exemplary embodiment of the present invention, the target gene comprises the epidermal growth factor receptor (EGFR). In such embodiments, the siRNA has substantial or complete identity to at least a portion of the EGFR gene. Using the nanogel systems of the present invention, EGFR expression can be reduced for at least 48 hours, for at least about 72 hours, for at least about 96 hours, or for at least about 120 hours.

The active agent is contained substantially within the nanogel. The active agent may be loaded into the nanogel by many methods know in the art including, but not limited to, swelling, emulsion, solvent evaporation, or in situ synthesis of the nanogel in the presence of the active agent. One of ordinary skill in the art would realize that the method for loading an active agent into a nanogel may depend upon several factors, such as polymeric composition of the nanogel, the composition of the active agent, and the composition of solvent or carrier in which the active agent is mixed, among others. In an exemplary embodiment of the present invention, an active agent is loaded into a nanogel by swelling of the nanogel. Regardless of the method of loading, the active agent is retained in the nanogel through non-covalent interaction between the active agent and the nanogel. These non-covalent interactions may include ionic bonds, hydrophobic interactions, hydrogen bonding, Van de Waals forces, Coulombic interactions, and the like.

A nanogel-based delivery system may further comprise a targeting moiety. As used herein, the term "targeting moiety" refers to a substance associated with the crosslinked polymer shell that enhances binding, transport, accumulation, residence time, bioavailability, or modifies biological activity of the nanogels or its associated active agent in a cell or in the body of a subject.

The targeting moiety can include, but is not limited to, an organic or inorganic molecule, peptide, peptide mimetic, proteins, antibodies, growth factors, enzymes, lectins, antigens or immunogens, viruses, viral vectors, receptors, ligands (e.g., folic acid), toxins, polynucleotides, oligonucleotides or aptamers, nucleotides, carbohydrates, sugars, lipids, glycolipids, nucleoproteins, glycoproteins, lipoproteins, steroids, hormones, growth factors, chemoattractants, cytokines, chemokines, a drug, among others.

In an exemplary embodiment of the present invention, the targeting moiety enhances binding, transport, accumulation, residence time, bioavailability, or modifies biological activity of the nanogels or active agents in a neoplastic cell or in the body of a subject having a neoplastic disease. Thus, the targeting moiety can have specificity for cellular receptors associated with neoplastic disease. For example, the targeting moiety can have specificity for the erythropoietin-producing hepatocellular (Eph) A2 receptor. In an exemplary embodiment of the present invention, the targeting moiety comprises a peptide having the amino acid sequence YSAYPDSVPMMSC (SEQ ID NO 1), referred to herein as the "YSA peptide." The YSA peptide mimics the ligand, ephrin-A1, which binds to the EphA2 receptor.

The targeting moiety can be coupled to the nanogel through the functionalization agent of the crosslinked polymeric shell. One of ordinary skill in the art would realize that selection of the targeting moiety may influence the selection of a functionalization agent as the method of coupling the targeting moiety to the crosslinked polymeric shell via the functionalization agent may depend on the chemical composition of the functionalization agent. For example, in embodiments of the present invention comprising the YSA peptide targeting moiety, the YSA peptide may be coupled to the crosslinked polymeric shell by EDC coupling of ε-maleimidocaproic acid to the primary amine of aminopropylmethacryamide in the crosslinked polymeric shell. As a result of coupling the targeting moiety to the crosslinked polymeric shell of the nanogel through the functionalization agent, the targeting moiety is displayed on at least a portion of the crosslinked polymeric shell.

An aspect of the present invention comprises a method of delivering an active agent into a cell, the method comprising: contacting a nanogel with a cell, the nanogel comprising a crosslinked polymer particle and an active agent contained substantially within the nanogel, wherein the active agent is non-covalently associated with the nanogel; and delivering an active agent to the cell.

Although not wishing to be bound by any particular theory, it is currently believed that contacting and delivering an active agent to a cell occurs through receptor-mediated endocytosis. In one embodiment of the present invention, the nanogel recognizes and binds a receptor on a cell surface. In an exemplary embodiment of the present invention, recognition and binding of a cell surface receptor is mediated by the targeting moiety associated with the crosslinked polymeric shell of the nanogel. Thus, the nanogel and its associated targeting moiety participate in a cell surface binding event, which is the initiating step to the cellular cascade associated with receptor-mediated endocytosis. The term "receptor-mediated endocytosis" generally describes a mechanism characterized by the binding of a ligand to a receptor disposed on the surface of a cell, where the receptor-bound ligand is internalized within a cell. Upon endocytosis of the nanogel, it is believed that the nanogel can escape the endosome and enter the cytosol to deliver the active agent by way of passive diffusion. Endosomal escape of the nanogels of the present invention appears to be an intrinsic property of the nanogel as not other substances are needed to facilitate endosomal escape of the nanogel and entry into the cytosol.

In an exemplary embodiment of a method for delivering an active agent to a cell, the active agent can comprise a siRNA. In such embodiments, the method for delivering an active agent to a cell can further comprise reducing expression of a target gene, wherein the siRNA has substantial sequence identity to the target gene. As used herein, the term "reducing expression of a target gene" refers to the ability of a siRNA to silence, reduce, or inhibit expression of a target gene. To determine extent of the reduction of expression of a target gene, examination of protein or mRNA levels associated with the target gene can be performed using techniques known to one of ordinary skill in the art, such as northern blots, Western blots, RTPCR, ELISA, and immunoprecipitation, among others. According to the embodiments of the present invention, silencing, inhibition, or reduction of expression of a target gene is achieved when the expression of the target gene is reduced about 95%, 90%, 85%, 80%, 75%, 70%, 65%, 60%, 55%, 50%, 45%, 40%, 35%, 30%, 25%, 20%, or 10% as compared to a cell or organism not exposed to the siRNA.

In one embodiment of a method for delivering an active agent to a cell, the nanogel can further comprise a targeting moiety and crosslinked polymer shell comprising a functionalization agent, the crosslinked polymer shell disposed substantially around the crosslinked polymer particle, wherein the targeting moiety is attached to the crosslinked polymer shell through the functionalization agent, and wherein the targeting moiety is displayed on at least a portion of the crosslinked polymer shell. In an exemplary embodiment, this method can further comprise reducing expression of a target gene, wherein the targeting moiety comprises a peptide having the amino acid sequence YSAYPDSVPMMSC (SEQ ID NO 1), and wherein the active agent is a siRNA having substantial sequence identity to the target gene, and wherein the target gene encodes epidermal growth factor receptor.

Another aspect of the present invention comprises a method for treating neoplastic disease comprising: administering to a subject having neoplastic disease an effective amount of a nanogel comprising a crosslinked polymer particle; a crosslinked polymer shell comprising a functionalization agent, wherein the crosslinked polymer shell is disposed substantially around the crosslinked polymer particle; a targeting moiety, wherein the targeting moiety is attached to the crosslinked polymer shell through the functionalization agent, and wherein the targeting moiety is displayed on at least a portion of the crosslinked polymer shell; and an active agent contained substantially within the nanogel, wherein the active agent is non-covalently associated with the nanogel.

The terms "subject," "individual" or "patient" are used interchangeably herein, and refers to a vertebrate, preferably a mammal, and more preferably a human. Mammals include, but are not limited to, primates, humans, cows, dogs, mice, rabbits, swine, rats, guinea pigs and equine. Tissues and cells are also encompassed by this terminology.

Systems and methods of the present invention contemplate treatment of a subject having neoplastic disease. Systems and methods of the present invention comprise administering an effective amount of a compound or composition to treat, ameliorate, or prevent neoplastic diseases in a subject. More specifically, systems and methods of the present invention comprise treatment of a human having neoplastic disease. Neoplastic disease may occur in many organs or tissues, including, but not limited to, bone, brain breast, cervix, colon, endometrium, esophagus, eye, gallbladder, kidney, liver, lung, lymphoid, mucosal, neuronal, ovary, pancreas, prostate, rectal, skin, stomach, and/or testicle, among others. The term "neoplastic disease" is intended to refer to hyperplasia, tumors, tumorigenesis, cancer, metastasis, cells that have uncontrolled growth, and the like. The systems and methods of the present invention may be used in combination with other treatments for neoplastic disease know in the art, including, but not limited to, surgery, radiation therapy, chemotherapy, and immunotherapy, among others.

Embodiments of the methods of treating neoplastic disease of the present invention comprise administering an effective amount of a nanogel. Administration of the nanogels may be performed by many known routes of administration, including, but not limited to, topical administration, oral administration, enteral administration, intratumoral administration, parenteral administration (e.g., epifascial, intraarterial, intracapsular, intracardiac, intracutaneous, intradermal, intramuscular, intraorbital, intraosseous, intraperitoneal, intraspinal, intrasternal, intravascular, intravenous, intravesical, parenchymatous, or subcutaneous administration), among others.

A "therapeutically effective amount" or "an effective amount" in the context of the present invention is considered to be any quantity of the active agent, which, when administered to a subject, causes prevention, reduction, remission, regression, or elimination of a neoplastic-related pathology. For example, in the context of cancer, "an effective amount" is considered to be any quantity of the one or more active agents, which, when administered to a subject causes prevention, reduction, remission, regression, or elimination of tumorigenesis and/or metastasis.

In embodiments of the present invention where the active agent is a siRNA, an "effective amount" or "therapeutically effective amount" of a siRNA can further include an amount sufficient to produce the desired effect, e.g., a decrease in the expression of a target sequence in comparison to the normal expression level detected in the absence of the siRNA.

The dosage of the active agent will depend on the condition being treated and the extent of the neoplastic disease, the particular active agent, route of administration, and other clinical factors such as weight and condition of the subject. siRNA may be provided in dosages ranging from about 0.001 µg/kg/day to about 1,000 mg/kg/day. Depending on the route of administration, the active agent administered and the toxicity associated with the nanogel-active agent system, a preferable dosage would be one that would yield an adequate blood level or tissue fluid level in the subject that would effectively cause prevention, reduction, remission, regression, or elimination of a neoplastic-related pathology.

In an exemplary embodiment of the present invention where the active agent is siRNA, a method of treating neoplastic disease can further comprise reducing expression of a target gene, wherein the siRNA has substantial sequence identity to the target gene. The target gen can encode a gene product relevant to neoplastic disease including but not limited to an anti-apoptotic molecule, a growth factor, a growth factor receptor, a mitotic spindle protein, a cell cycle protein, an angiogenic factor, an oncogene, an intracellular signal transducer, a molecular chaperone, among others. In an exemplary embodiment of the present invention, the target gene encodes epidermal growth factor receptor.

In yet another embodiment of a method of treating a neoplastic disease, the method can further comprising increasing sensitivity of the subject to a chemotherapeutic agent. The chemotherapeutic agents can be one or more of many chemotherapeutic agents known in the art including, but not limited to taxane chemotherapy, such as paclitaxel and docetaxel. As used herein "increased sensitivity to a chemotherapeutic agent" refers to an increase in susceptibility (or conversely a reduction in chemoresistance) of a neoplastic-related pathology to a chemotherapeutic agent upon exposure to the siRNA as compared to the level of sensitivity to a chemotherapeutic agent in the absence of the siRNA.

It must be noted that, as used in this specification and the appended claims, the singular forms "a," "an," and "the" include plural referents unless the context clearly dictates otherwise.

All patents, patent applications and references included herein are specifically incorporated by reference in their entireties.

Throughout this description, various components may be identified as having specific values or parameters, however, these items are provided as exemplary embodiments. Indeed, the exemplary embodiments do not limit the various aspects and concepts of the present invention as many comparable parameters, sizes, ranges, and/or values may be implemented. It should be understood, of course, that the foregoing relates only to exemplary embodiments of the present invention and that numerous modifications or alterations may suggest themselves to those skilled in the art without departing from the spirit and the scope of the invention as set forth in this disclosure.

The present invention is further illustrated by way of the examples contained herein, which are provided for clarity of understanding. The exemplary embodiments should not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Therefore, while embodiments of this invention have been described in detail with particular reference to exemplary embodiments, those skilled in the art will understand that variations and modifications can be effected within the scope of the invention as defined in the appended claims. Accordingly, the scope of the various embodiments of the present invention should not be limited to the above discussed embodiments, and should only be defined by the following claims and all equivalents.

EXAMPLES

Example 1

Peptide-Fiunctionalized Nanogels for Targeted siRNA Delivery

The present Example is directed to drug delivery systems and methods that employ the synthetic hydrogel nanoparticle (nanogel). Nanogels possess a high degree of porosity, permitting a high payload capacity and can also be selectively surface functionalized to enable tumor-specific targeting. Thus, we have developed straightforward, scalable syntheses of surface-functionalized, ~100-nm diameter, core/shell nanogels composed of poly(N-isopropylmethacrylamide) (pNIPMAm), an amphiphilic polymer that is strongly hydrated at physiological temperature and is likely therefore to resist protein adsorption relative to more hydrophobic carriers. This polymer has also garnered interest due to its dramatic thermoresponsivity; it undergoes an entropically driven coil-to-globule (swollen-to-collapsed) transition at ~43° C., which may have utility for thermally-triggered delivery. However, in the present Example, this thermoresponsivity is only used to enable the synthesis of monodispersed core/shell nanogels via precipitation polymerization, as we have discussed previously in Jones, C. D., and Lyon, L. A. (2000) Synthesis and Characterization of Multiresponsive Core-Shell Microgels. *Macromolecules* 33, 8301-8306, and Blackburn, W. H., and Lyon, L. A. (2008) Size-controlled synthesis of monodisperse core/shell nanogels. *Colloid Polym. Sci.* 286, 563-569.

The core/shell pNIPMAm nanogel construct used to encapsulate and deliver siRNA to ovarian cancer cells is illustrated in FIG. 1. A 12 amino acid peptide (YSAYPDS-VPMMS or "YSA") (SEQ ID NO 1) was coupled to surface of ~100-nm diameter core/shell nanogels to permit cell-specific targeting and subsequent delivery of high concentrations of siRNA to the target cells. The YSA peptide mimics the ligand ephrin-A1, which binds to the erythropoietin-producing hepatocellular (Eph) A2 receptor. In addition to specific expression in neovasculature, EphA2 is highly expressed by a number of tumor cells including those derived from ovarian, prostate, breast, and colon cancers, making it an excellent target for tumor-specific delivery. Thus, we demonstrate herein that pNIPMAm nanogels have a high loading capacity for siRNA, and that these nanogels are delivered to the cytoplasm of ovarian cancer cells via ligand-receptor binding mediated endocytosis. Importantly, cytotoxicity was not observed to arise from the nanocarrier, suggesting that this approach could be a highly efficacious one. In addition, delivery of siRNA to cells in culture can be performed in the presence of serum suggesting that nanogels may be of particular advantage for in vivo delivery.

Material and Methods. All materials were purchased from Sigma-Aldrich (St Louis, Mo.) and used as received unless otherwise noted.

Nanogel core synthesis. Nanogel core particles were synthesized by free-radical precipitation polymerization, as discussed in Blackburn, W. H., and Lyon, L. A. (2008) Size-controlled synthesis of monodisperse core/shell nanogels. *Colloid Polym. Sci.* 286, 563-569. The use of thermally phase separating polymers enables the use of precipitation polymerization for the synthesis of highly monodispersed nanogels. The molar composition was 98% N-isopropylmethacrylamide (NIPMAm), 2% N,N'-methylenebis(acrylamide) (BIS), with a total monomer concentration of 140 mM. The solution also contained a small amount (~0.1 mM) of acrylamidofluorescein (AFA) to render the nanogels fluorescent for visualization via confocal microscopy. In a typical synthesis, 100 mL of a filtered, aqueous solution of NIPMAm, BIS, and sodium dodecyl sulfate (SDS, 8 mM total concentration) was added to the reaction flask, which was then heated to 70° C. The solution was purged with $N_2$ gas and stirred vigorously until the temperature remained stable. The AFA was added, and after 10 minutes the reaction was initiated by the addition of a 1 mL solution of 800 mM ammonium persulfate (APS) to make the final concentration of APS in the reaction ~8 mM. The solution turned turbid, indicating successful initiation. The reaction was allowed to continue for 4 h under an $N_2$ blanket. After synthesis, the solution was filtered through Whatman filter paper to remove a small amount of coagulum.

Nanogel shell synthesis. The core nanogels described above were used as seeds for the addition of a hydrogel shell in a seeded precipitation polymerization scheme. Briefly, 10 mL of the core nanogel solution and 0.0577 g SDS were first added to a three-neck round-bottom flask and heated under $N_2$ gas to 70° C. A 50 mM monomer solution with molar ratios of 97.5% NIPMAm, 2% BIS, and 0.5% aminopropylmethacrylamide (APMA, Polysciences, Warrington, Pa.) was prepared in 39.5 mL of $dH_2O$. The solution was added to the three-neck round-bottom flask, and the temperature was stabilized at 70° C. while continuously stirring. The reaction was initiated by a 0.5 mL aliquot of 0.05 M APS. The reaction proceeded for 4 h under $N_2$ gas. Following the synthesis, the solution was filtered through Whatman filter paper, and the nanogels were purified by centrifugation followed by resuspension in $dH_2O$.

Nanogel characterization. Multi-angle laser light scattering (MALLS) (Wyatt Technology Corporation, Santa Barbara, Calif.) detection following asymmetric field flow fractionation (AFFF) was used to determine the distribution of z-average radii ($R_z$) for all nanogels. For all separations, a cross-flow of 0.30 mL/min was used with a channel flow of 1.0 mL/min The MALLS detector is equipped with a Peltier device to maintain a flow cell temperature of 25° C. and collects scattered light from 16 different fixed angles to determine the $R_z$ of the nanogels. By measuring $R_z$ as a function of elution time, we constructed a chromatogram that permits the determination of the weight fraction of nanogels as a function of radius, thereby providing a sample polydispersity. ASTRA 5.1.5.0 software was used to determine $R_z$ values using the Debye fit method. The core/shell nanogels synthesized using the methods described above were determined to have $R_z$ values of ~54 nm with size polydispersities of <10 as representative AFFF/MALLS data are shown in FIG. 2.

Characterization of the refractive increment (dn/dc) of nanogels was performed to determine particle molecular weight by static light scattering. Differential refractive index analysis (dRI, OptiLab rEX, Wyatt Technologies, Inc.) was performed in batch mode. To ensure accurate data, the refractive index was calibrated prior to each measurement using sodium chloride concentrations ranging from 0.1 mg/mL to 15.0 mg/mL. All nanogel dilutions were prepared in dust-free vials, which were rinsed sequentially with deionized water, absolute ethanol, and HPLC-grade acetone. Nanogels were resuspended in distilled, deionized water over a concentration range from $2.5 \times 10^{-6}$ g/ml to $3.75 \times 10^{-4}$ g/mL. The use of MALLS in conjunction with the rEX differential refractometer permitted the measurement of the z-average molecular mass ($M_z$) from the determined dn/dc values and the angle dependent light scattering data.

YSA synthesis. The YSA peptide (YSAYPDSVPMMSC) (SEQ ID NO 1) was synthesized using standard Fmoc chemistry as described in Clark, K. D., Volkman, B. F., Thoetkiattikul, H., King, D., Hayakawa, Y., and Strand, M. R. (2001) Alanine-scanning mutagenesis of plasmatocyte spreading peptide identifies critical residues for biological activity. *J. Biol. Chem.* 276, 18491-6. Following synthesis, the peptide was cleaved from the resin and deprotected for 4 h in reagent K after air-drying. The peptide was purified using a series of 5 mL injections onto a preparatory HPLC column (10-m; particle size, 21.2 mm 25 cm, Jupiter C18; Phenomenex Inc., Torrance, Calif.) using HPLC-grade $H_2O$ and a linear gradient of acetonitrile (0-70 min, 10-80%) at 5 mL per min Both the acetonitrile and $H_2O$ contained 0.05% trifluoroacetic acid. The desired peak was identified by matrix-assisted laser desorption ionization time-of-flight mass spectrometry, and the peaks from multiple runs were pooled, lyophilized, and stored at 4° C. in solid form. A scrambled form (SCR) of the YSA peptide (DYPSMAMYSPSVC) (SEQ ID NO 2) was also synthesized via this method for use as a control. On other occasions, the YSA and SCR peptides were purchased from GenScript Corp (Piscataway, N.J.).

Peptide conjugation. In this sExample, a maleimide-functionalized nanogel was produced through the EDC coupling of ε-maleimidocaproic acid (EMCA) to the primary amines in the shell of the nanoparticle. As described in the nanogel shell synthesis, primary amines were introduced through the copolymerization of APMA (0.5% molar ratio). Given that APMA is efficiently incorporated at these low molar ratios, the amine equivalents available for bioconjugation can be estimated (~$2.2 \times 10^{-6}$ amines per 88.3 mg of lyophilized particles). From this estimate, peptide coupling was performed by introducing YSA peptide in a 1:1 molar ratio with amine (YSA molecular weight=1450.66 g/mol). The YSA peptide was then conjugated to the nanogels via maleimide coupling to the cysteine residue on the C-terminal end of the peptides.

First, 88.3 mg of nanogels (~$2.2 \times 10^{-6}$ amine equivalents) was resuspended in 35.0 mL of pH 6.0 MES buffer and allowed to shake for 2 hours. A second solution was prepared where $4.4 \times 10^{-6}$ moles (0.68 mg) of 1-ethyl-3-methyl-(3-dimethylaminopropyl) carbodiimide (EDC, Pierce, Rockford, Ill.), $4.4 \times 10^{-6}$ moles (0.96 mg) N-hydroxysulfosuccinimide (NHSS) and $2.2 \times 10^{-6}$ moles (0.46 mg) of EMCA were dissolved in 3.0 mL of pH 6.0 MES buffer. This solution was reacted for 30 min at room temperature to activate the EMCA acid groups, which permits amide coupling to take place between the EMCA acid groups and the amines on the nanogel surface. This activated EMCA solution was then added to the nanogel solution and reacted for 2 h on a shaker table. The nanogels were centrifuged 3 times to remove any unreacted material, with resuspension in pH 6.0 MES buffer following each centrifugation. Finally, 3.2 mg of the appropriate peptide was added to the activated nanogels and reacted overnight. Peptide-functionalized nanogels were purified by centrifugation and resuspended in distilled, deionized water.

The number of bioconjugated YSA targeting peptides per particle was estimated by considering the number of primary amines available for conjugation and the number density of nanogels used during bioconjugation (as measured by static light scattering). Through differential refractometry, the nanogel refractive increment was determined to be 0.176±0.002 mL/g Measurement of z-average molecular weight through multi-angle static light scattering provided the z-average mass of non-conjugated particles, $M_z = 2.19 \times 10^7$ g/mol (1° Debye fitting, 0.1% fit error). Thus, a total mass of 88.3 mg of lyophilized particles used during conjugation is equivalent to $2.43 \times 10^{15}$ particles. Assuming a 50% peptide conjugation efficiency and $2.2 \times 10^{-6}$ amine equivalents available for bioconjugation, a conservative estimate of peptide density is ~225 YSA peptides/particle.

In vitro siRNA encapsulation and release. Our group employs a "breathing-in" method for the encapsulation of various macromolecules within nanogels. In a typical method, lyophilized nanogels are resuspended in an aqueous solution containing the macromolecule to be loaded. Importantly, this is done using a loading solution volume that is almost completely imbibed by the swelling nanogels. In this fashion, the hydrogel network imbibes the payload with high efficiency and without relying on simple equilibrium partitioning to determine the maximum loading level. To determine the rate of siRNA release from nanogels loaded in this fashion, a mixture of oligonucleotide was prepared containing 0.250 mL of 20 μM siGLO red transfection indicator and 1.00 mL of 20 μM siGENOME Lamin A/C control siRNA (Dharmacon, USA). Particles were resuspended in this mixture at a concentration of 4 mg per 250 μL siRNA solution. This concentration of particles is near the solubility limit for the nanogels in PBS, ensuring a high degree of solvent and solute uptake into the hydrogel network. The particles were allowed to resuspend for 12 hours at room temperature while shaking.

The encapsulation efficiency was determined via ultracentrifugation of the nanogel loading solution and measurement of supernatant siRNA concentration by UV-vis spectroscopy (Shimadzu UV-1601). The moles of siRNA in the loading solution ($m_{siRNA, Loading}$) and in the supernatant ($m_{siRNA, Supernatant}$) were determined via interpolation from a separately constructed standard curve of absorbance vs. concentration ($R^2 > 0.99$). The encapsulation efficiency (EE) of the system could then be calculated through analysis of the amount of siRNA in the loading solution and the remaining moles of siRNA in the supernatant after nanogel swelling was complete, as illustrated by Equation 1 and in similar encapsulation experiments.

$$EE = \frac{m_{siRNA,Loading} - m_{siRNA,Supernatant}}{m_{siRNA,Loading}} \times 100 \quad (1)$$

The release of solutes from nanogels was performed in 10% serum to simulate physiological conditions. Release experiments were performed by dispersing 200 μL of loaded nanogels in 2.20 mL of 0.01 M phosphate buffered saline containing 10% fetal bovine serum (equilibrated at 37° C.) in 3.2 mL polycarbonate centrifuge tubes (Beckman Coulter, USA). The nanogel suspension was allowed to incubate at 37° C. while shaking. At specific time points, the tubes were centrifuged for 90 mM at 687 000×g (at 37° C.), and an aliquot of supernatant (0.75 mL) was removed for UV-vis analysis. This volume was replaced with fresh buffer. Upon centrifugation, the gel pellet had a homogenously distributed bright pink color, indicating significant retention of siRNA throughout the experiment. The cumulative siRNA released was calculated by calculating the total moles detected in the supernatant as a function of time, as described in Equation 2.

$$\text{Cumulative siRNA Released} = \frac{m_{TOTAL siRNA,Supernatant}}{m_{siRNA,Loading}} \times 100 \quad (2)$$

All release studies were performed in triplicate for statistical analysis, using identical nanogel loading and release conditions.

Zeta-potential determination. Excluding the 0.5 mol % APMA copolymerized into the shell of our nanogel particles, the nanogels are composed of largely non-ionic monomers. To confirm their suspected electroneutrality, which should be critical for reducing non-specific cell and protein interactions, the zeta-potential of both YSA-conjugated and non-conjugated core/shell nanogels were measured (Zeta-Sizer Nano, Malvern, U.K.). All nanoparticles used in this investigation demonstrated zeta-potential values <+0.300 mV, suggesting that they are only weakly charged and should therefore not interact strongly with serum proteins or cell surfaces via Coulombic forces.

Cell culture. Hey cells were provided by Gordon W. Mills, Department of Molecular Therapeutics, the University of Texas, M.D. Anderson Cancer Center. Hey cells were cultured in RPMI 1640 (Mediatech, Manassas, Va.) supplemented with 10% v/v heat-inactivated fetal calf serum (Invitrogen), 2 mM L-glutamine (Mediatech), 10 mM HEPES buffer (Mediatech), penicillin (100 U/ml), and streptomycin (100 µg/mL). The BG-1 cell line was provided by Julie M. Hall and Kenneth S. Korach, Receptor Biology Section, Laboratory of Reproductive and Developmental Toxicology, National Institute of Environmental Health Sciences, NIH, Division of Intramural Research, Environmental Disease and Medicine Program, Research Triangle Park, N.C. BG-1 cells were propagated in DMEM:F12/50:50 (Mediatech) supplemented with 10% v/v heat-inactivated fetal calf serum, penicillin, and streptomycin.

siRNA encapsulation for cell studies. Using the "breathing-in" method for encapsulation (as described above), dried nanogels were reswollen in the presence of the siRNA, thereby imbibing the solute within the hydrogel network. In a typical procedure for in vitro cell delivery, a 20 µM solution (250 µL) of a fluorescent siRNA transfection indicator, siGLO (Dharmacon), or EGFR siRNA (Dharmacon, Lafayette, Colo.) was prepared in phosphate buffered saline (PBS). Lyophilized nanogels were dissolved in the siRNA solution at a concentration of 4 mg in 250 µL and allowed to shake overnight at room temperature. Importantly, this nanogel concentration results in nearly all of the solvent being taken up by the nanogels. This volume-filling approach ensures a maximal uptake of siRNA within the nanogels. After shaking, the nanogels were centrifuged to remove any free siRNA and resuspended in PBS. A standard curve for increasing concentrations of siRNA was made by measuring the absorbance at 260 nm using a Shimadzu UV 1601 spectrophotometer. After siRNA was encapsulated in the nanogels, they were centrifuged, and the absorbance of the supernatant was measured to determine the amount of incorporated siRNA.

Cell transfection using nanogels. Hey or BG-1 cells were plated onto an 8-well chamber slide ($5\times10^3$ cells/well), and the cells allowed to adhere overnight at 37° C. in a 5% $CO_2$ atmosphere. After washing the wells with PBS and replacing the media, siGLO-loaded/YSA-conjugated nanogels, unloaded YSA-conjugated nanogels, pNIPMAm nanogels, or siGLO only were added to wells. Cells were incubated in each case for 4 h. In experiments where preincubation of ephrin-A1 was used to initiate internalization and degradation of EphA2, ephrin-A1 was added to the media at a final concentration of the ligand of 2 µg/mL. After incubation, the cells were washed with PBS, and the medium replaced. For fixation prior to confocal imaging, the cells were incubated with 2% (v/v) paraformaldehyde for 30 min Immunoblotting. Hey cells were plated into 6-well plates ($5\times10^5$/well) and allowed to adhere overnight at 37° C., 5% $CO_2$. The cells were lysed with 100 µL of lysis buffer (50 mM Tris-HCl, pH 7.5, 150 mM NaCl, 2 mM EDTA (Fisher), 2 mM EGTA (Fisher), 1 mM sodium orthovanadate, 2.5 mM sodium pyrophosphate, 1 mM β-gycerolphosphate, 1 mM phenylmethanesulfonyl fluoride, 10 µg/mL aprotinin, 10 µg/mL leupeptin, 1% Triton X-100, and 5% glycerol), and the cell lysates sonicated four times for five seconds each. The lysates were cleared by centrifugation at 11,000×g rcf for 15 mM at 4° C. Cell lysates were prepared for analysis by the addition of an equal volume of Laemmli 2× sample buffer. The samples were heated to 95° C. for 5 mM to denature the proteins. The proteins were separated on a 10% SDS-PAGE gel and transferred onto nitrocellulose. The blots were blocked with either 5% nonfat dry milk (NFDM) or 5% bovine serum albumin (BSA) in 10 mM Tris-buffered saline, pH 7.5 plus 1% Tween 20 (TBST, BioRad) for 1 hour at room temperature. The blots were probed with anti-EGFR antibody (Cell Signaling, Danvers, Mass.; cat. no. 4405) or with a β-actin antibody (Millipore, Billerica, Mass.; Mab1501) diluted in 5% NFDM or 5% BSA overnight, with shaking at 4° C. For EphA2 detection, the blots were probed with an anti-EphA2 polyclonal antibody (Santa Cruz Biotechnology, Santa Cruz, Calif.; sc-294). The blots were washed three times with TBST and probed with goat anti-rabbit IgG (Santa Cruz, sc-2004) or with goat anti-mouse IgG (Santa Cruz, sc-2005) linked to horseradish peroxidase (HRP). Bands were visualized on film (Pierce) using the ECL reagent, SuperSignal West Pico™ (Pierce).

Confocal microscopy. A Zeiss LSM510 confocal microscope was used to take cell images. Cells were incubated with nanogels for 4 h. After 4 h, the cells were washed and then fixed on the slide. An $Ar^+$ laser was used to excite the AFA-labeled nanogels, whereas a HeNe laser was used to excite the fluorescently labeled siGLO. LSM510 software was used to view the images.

Flow cytometry. Hey cells were plated at $2.5\times10^5$ cells/well in a 12-well, cell culture plate. Cells were allowed to adhere overnight in an incubator at 37° C. in a 5% $CO_2$ atmosphere. Cells were washed, and fresh medium was added containing YSA-pNIPMAm or SCR-pNIPMAm nanogels at a concentration of 0.8 mg/mL and incubated for four hours. Following incubation, the cells were washed with PBS and removed from the plate by Trypsin-EDTA treatment. The cells were washed with PBS and fixed with 2% (v/v) paraformaldehyde. Cells were analyzed using a LSR Flow Cytometer (BD Biosciences). Data analysis was carried out using FlowJo software.

Toxicity Studies—Trypan blue exclusion assay. Hey cells were plated onto an 8-well chamber slide ($1\times10^4$ cells/well) and allowed to adhere overnight at 37° C. and 5% $CO_2$. The media was removed, the wells washed with PBS, and the medium replaced. PNIPMAm nanogels, YSA-conjugated nanogels, and SCR-conjugated nanogels were added to cells and incubated for 72 h. Untreated cells were used as controls. After 72 h, the cells washed with PBS, and a 1:1 solution of trypan blue was added to each well. After 1 min, the trypan blue was removed, the cells were washed with PBS, fixed with 2% (v/v) paraformaldehyde, and air dried. Each well was then viewed via bright field microscopy to determine the number of stained (dead) versus unstained cells. Five fields were viewed for each treatment.

Toxicity Studies—Tox 8 assay. Hey cells were plated onto 96-well plates ($1\times10^4$ cells/well) and allowed to adhere overnight at 37° C. and 5% $CO_2$. The media was removed, and the cells were washed with PBS followed by replacement of the medium. Cells incubated with EGFR siRNA-loaded YSA-labeled nanogels, unloaded YSA-labeled pNIPMAm nanogels, unlabeled pNIPMAm, or YSA peptide alone were tested using this assay. The cells were incubated under all conditions for 4 h. The cells were then washed with PBS, the medium replaced, and the cells incubated for an additional 72 h in medium. The Tox 8 reagent (Sigma) was added to the cells according to the manufacturer's instructions. The absorbance at 600 nm was read after 1 hour, and the extent of cellular viability/proliferation determined Results. The nanogels described in this contribution were developed around two main design criteria, as depicted in FIG. 1. For this application, both peptide-based targeting of ovarian cancer and efficient encapsulation and delivery of RNA inhibitors (RNAi's) are required. The core/shell nanogels synthesized using the methods described above were determined to have $R_z$ values of ~54 nm with size polydispersities of <10%, as described previously. Representative AFFF/MALLS chromatograms for both the core and core/shell nanogels are shown in FIG. 2. To determine the timescale for retention of siRNA within the pNIPMAm nanogels, siRNA leakage was investigated using simulated physiological conditions. As described above, nanogels were loaded using a model mixture of siRNA, containing both the siGLO red transfection indicator and the siGENOME Lamin control. The nanogel was observed to encapsulate the siRNA with high efficiency (93±1%), which is equivalent to a loading level of 1.6 wt % or 16 µg siRNA/mg of nanogels. As shown in FIG. 3, only ~33% of the siRNA is observed to leak from the nanogels within the first 12 hours (67% retained). Indeed, this approximate level of retention persists out to 35 hours, suggesting very efficient entrapment of the siRNA within the nanogel network. Retention of this magnitude is promising for intravenous oligonucleotide delivery given previously determined timescales (~6 hours) for extravasation via the enhanced permeability and retention effect.

To establish the efficacy of targeting in vitro, the uptake of nanogels by two ovarian cancer cell lines, Hey and BG-1, was determined We previously demonstrated high expression of EphA2 by Hey cells and low expression of the receptor by the BG-1 cell line. Because of these differences in EphA2 expression, we expected to see higher levels of nanogel uptake via receptor-mediated endocytosis with Hey cells as compared to BG-1 cells. Furthermore, we expected that the degree of siRNA delivery to those cells would be dependent on the cell type and the presence of the peptide ligand. To load siRNA into the nanocarrier, lyophilized nanogels were loaded with siGLO (a fluorescently-labeled siRNA delivery tracker) by reswelling them in a concentrated solution of the siRNA, as described above. To obtain a relative concentration of the siGLO taken up by the nanogels, absorbance measurements were compared to a standard curve of siGLO in solution ($R^2$>0.99). We determined in a series of three trials that 80-95% (by mass) of the siGLO was incorporated into the nanogels by this method, in agreement with the loading levels calculated in the release kinetics experiment described above.

Following loading with siGLO, nanogels were incubated with either Hey (high EphA2 expression) or BG-1 (low EphA2 expression) cells in order to compare the levels of targeted uptake by ovarian cancer cells. Uptake of the nanogels into the cells was followed using a fluorescent tag (AFA) incorporated into the nanogel core as well as by the fluorescence of the siGLO. In previous studies, we determined that high levels of nanogel uptake by cells occurred after four hours. As a result, cells were incubated for four hours with siGLO-loaded/YSA-conjugated nanogels to monitor specific targeting to EphA2. Unloaded YSA-conjugated nanogels, non-targeted pNIPMAm nanogels, and siGLO only were used as controls, with identical 4-hour incubation times. In all experiments described in this Example, we maintained a constant nanogel/cell ratio of 1 mg nanogels/$5 \times 10^5$ cells. For siRNA-loaded nanogels, this corresponds to 16.6 µg siRNA/$5 \times 10^5$ cells. After incubation, the cells were washed, and the slides fixed for confocal microscopy imaging. FIG. 4a shows that Hey cells targeted with YSA-conjugated nanogels have high levels of nanogel uptake as indicated by the presence of green fluorescence. At this time point, siGLO was retained at high levels within the internalized nanogels as indicated by the cell-localized red fluorescence. Merging of the two fluorescence channels showed strong overlap, further indicating delivery of the siGLO by the nanogels into the Hey cells. Hey cells incubated with YSA-targeted but unloaded nanogels showed strong green fluorescence, indicating cell uptake. A small amount of non-targeted uptake was observed for nanogels lacking the YSA peptide. Note that it was extremely difficult to find evidence of nonspecific uptake, and the fluorescence shown in the figure represents the appearance of the rare uptake event observed, and does not represent the overall fluorescence from the entire population of cells. When Hey cells were incubated with siGLO alone, no cell-localized red fluorescence was detected; this is expected since RNA does not easily permeate the cell membrane in the absence of a carrier vehicle.

Targeting experiments were also performed using low EphA2 expressing BG-1 cells (FIG. 4b). Decreased levels of green fluorescence were observed in BG-1 cells when compared to the fluorescence observed in the Hey cell cultures. The lower amount of nanogel uptake by the BG-1 cells was most likely due to the reduced EphA2 receptor expression; we have demonstrated a ~2.5-fold difference in EphA2 expression levels between these two cell lines. Control studies using non-targeted pNIPMAm nanogels or siGLO only showed no fluorescence in either the green or red fluorescent channels. These results indicate that the YSA peptide imparts targeting properties to the nanogels in the case of both the high (Hey) and low (BG-1) EphA2 expressing cells, and that the amount of nanogel uptake was dependent upon the level of EphA2 receptor expression. These results also indicate that nonspecific or non-targeted uptake of nanogels by cultured cells is low, and that the siRNA is unable to penetrate the cell membrane in the absence of a carrier vehicle. Together, these initial results illustrate the promise of the targeted nanogel construct for targeted delivery of oligonucleotide cargo.

To further establish the mechanism of nanogel targeting and uptake, we took advantage of the known receptor internalization properties of the EphA2 receptor. Specifically, it has been shown that binding of ephrin-A1, a ligand for EphA2, to EphA2 receptor causes internalization and degradation of the receptor-ligand complex. FIG. 5 shows the results of studies wherein this receptor recycling process was used to establish the nanogel target by preincubating Hey cells with ephrin-A1 before YSA-targeted nanogel incubation. We hypothesized that if uptake of nanogels is EphA2 receptor-mediated, YSA-targeted uptake after cell exposure to ephrin-A1 should be reduced, as the EphA2 receptor will be internalized and less available for binding to the nanogels. Hey cells were incubated overnight in an 8-well chamber slide. Two µg/mL of ephrin-A1 were added, and the cells were incubated for 1 hour at 37° C. After ephrin-A1 incubation, siGLO-loaded/YSA-conjugated nanogels were added to both ephrin-A1 and control (PBS) treated wells. The cells were incubated for four hours, washed, and processed for imaging. FIG. 5 shows the nanogel uptake in Hey cells preincubated with ephrin-A1. Whereas these cells (top three panels) show some uptake of nanogels and encapsulated siGLO, the amount of uptake is greatly diminished compared with untreated cells (lower three panels). These results suggest that YSA-conjugated uptake by Hey cells is conducted to a large extent through EphA2, however, a small amount of uptake may occur through nonspecific mechanisms or via binding of YSA to other Eph receptors. This is not surprising, given the fact that ephrin and various small molecule ephrin mimics display binding affinities for multiple receptors of the Eph family. Flow cytometry was also used to establish the EphA2-associated binding of the peptide-targeted nanogels. In this case, a scrambled (SCR) peptide sequence (DYPS-MAMYSPSVC) possessing the same amino acid composition of the YSA peptide was tethered to the nanogels. The resultant nanogels should therefore possess the same physicochemical surface properties as the YSA-labeled nanogels, but should not specifically bind to the EphA2 receptor. FIG. 6 shows the results of these studies, where cells incubated with YSA-labeled nanogels display ~10-fold greater fluorescence relative to those incubated with SCR-labeled nanogels. Furthermore, the fluorescence signal associated with cells incubated with SCR-labeled nanogels is only slightly greater than the cell autofluorescence background signal.

The effect of nanogels on tumor cell toxicity and proliferation was examined using two cell viability assays. For the trypan blue exclusion assay, Hey cells were incubated with pNIPMAm nanogels, YSA-conjugated nanogels, or SCR-conjugated nanogels for 72 hours. The cells were then washed with PBS, and trypan blue was added to the cells. Five fields were observed via microscopy for each treatment group. Blue cells, indicating dead cells, were not observed in any of the fields examined for any of the treatment groups (data not shown). To more precisely establish any negative effects associated with nanogel-based delivery, we used the Tox 8 viability proliferation assay. Hey cells were incubated in 96-well plates overnight and nanogels delivered and removed via the usual method. In the gene silencing data shown below, we chose siRNA targeting epidermal growth factor receptor (EGFR); knockdown of this receptor is non-lethal, but has clinical relevance in the treatment of drug resistant ovarian carcinomas. This siRNA was therefore used in these toxicity studies, as well. Again, we maintained a ratio of 1 mg nanogels/$5 \times 10^5$ cells for all samples. For the EGFR siRNA-loaded nanogels, this corresponds to 16.6 µg siRNA/$5 \times 10^5$ cells. Wells were washed with PBS, and 100 µL of cell culture medium was added to the wells. After 72 hours, Tox 8 was added to the cells according to the manufacturer's instructions, and the cell viability was determined spectrophotometrically. This analysis (FIG. 7) revealed no significant difference for any treatment when compared with control (untreated) cells, although exposure to non-targeted nanogels and siRNA-containing nanogels showed slight decreases in viability; the origin of this effect is currently under investigation. These results indicate that treatment of Hey cells with targeted nanogels does not greatly inhibit cell proliferation, indicating limited toxicity of the nanogels under these conditions.

These promising studies clearly illustrate the efficacy of peptide-targeted delivery of siRNA cargos via nanogel carriers. The lack of toxicity observed is of particular interest, given the high toxicity observed for some cationic lipid-based siRNA targeting methods, which limits the maximum doses that can be delivered, and also compromises the potential for in vivo delivery. In the present studies, a ratio of 16 µg siRNA or 1 mg nanogels/$5 \times 10^5$ cells was used throughout without significant toxicity being observed. These concentrations are somewhat higher than those suggested for common commercial regents such as RNAiFect (Qiagen) or DharmaFECT (Dharmacon), suggesting that the nanogel approach is capable of delivering siRNA amounts at or above those achievable by optimized commercial reagents. Another complicating factor in current methodologies is the frequent need for cellular delivery under serum free conditions; serum lipids and proteins compromise the stability of many liposomal formulations making their efficacy significantly lower. In the studies described herein, we have illustrated that delivery of siGLO is excellent in serum-containing medium, further establishing the promise of this construct.

As a final preliminary test of the efficacy of the approach, we performed a limited investigation of siRNA-based silencing. Clearly, any delivery approach must deliver functional siRNA to the cell interior in order for it to be truly useful. If the nanogel carrier were unable to protect the cargo against degradation in the endosomal or lysosomal compartments, or if the nanogels were unable to escape from endosomes in order to deliver the siRNA to the cytosol, the amount of RNAi would be very low. Thus, we have undertaken a preliminary study of gene silencing to illustrate a minimal requirement for siRNA delivery: the functional silencing of a target mRNA.

As described above, we chose siRNA targeting EGFR; knockdown of this receptor is non-lethal, but has clinical relevance in the treatment of drug resistant ovarian carcinomas. To determine if we could effectively knockdown EGFR in vitro, EGFR siRNA was encapsulated at a concentration of 16.6 µg of EGFR siRNA/mg of nanogels, using the loading technique described above. Nanogels were then added to Hey cells (1 mg of nanogels or 16.6 µg siRNA/$5 \times 10^5$ cells) and incubated at 37° C. for four hours. The unincorporated nanogels were then removed by washing the cells, and the medium was replaced. Controls included cells incubated with siRNA-loaded but non-targeted pNIPMAm nanogels, unloaded YSA-targeted nanogels, pNIPMAm nanogels, and untreated cells. All cells were harvested at 48 hours and assayed for EGFR expression by immunoblotting. FIG. 8 shows the results of this experiment; a significant reduction in EGFR expression is observed under these conditions relative to all controls ($p<0.01$ relative to untreated sample by paired t-test, $n=3$). A small, statistically insignificant decrease in EGFR expression was noted in the unloaded, YSA-targeted nanogel control ($p>0.1$). If this observation is indeed a real one, it may be due to cross talk between the EGFR and the EphA2 receptors, as described by Larsen and colleagues. In addition, a small decrease in EGFR expression was observed when cells were incubated with pNIPMAm nanogels alone, although the difference is not statistically significant ($p>0.3$) in light of the large observed variability in expression.

These preliminary results illustrate that the targeted nanogels are capable of functional delivery of siRNA to ovarian carcinomas without overt toxic effects, and that the subsequently internalized siRNA is available for gene silencing.

Conclusions. Peptide-labeled nanogels with a high loading capacity for siRNA have been developed and can be effectively targeted to ovarian carcinomas by receptor-peptide binding. The encapsulated siRNA is transported into the cell interior, where it is available for gene silencing, as illustrated in this case by EGFR knockdown. Since the locus of siRNA-mediated gene silencing is the cytosol, the results are suggestive of the surprising conclusion that endosomal uptake of the nanogels is followed by endosomal escape, resulting in efficient transport/release of the siRNA to the cytosol; however, we do not currently know the exact mechanism by which endosomal escape occurs. It is plausible that the nanogels respond to endosomal changes in osmotic pressure and ionic strength by undergoing a volume change. This phenomenon, called osmotic swelling/deswelling is fundamental to the phase behavior of gel networks and may serendipitously be responsible for the excellent delivery properties described above. In addition to the gene-silencing efficacy, the nanocarriers are demonstrated to be non-toxic under the conditions investigated and are effective even when delivered in serum-containing medium.

Example 2

Chemosensitization of Cancer Cells by SiRNA using Targeted Nanogel Delivery

Although a number of chemotherapeutic treatments have been shown to be effective at inhibiting or eliminating cancer cell growth in preclinical studies, clinical applications are often limited due to the toxic side effects associated with anticancer drugs. Patients are often unable to tolerate the level of a drug needed to effectively eliminate malignant cells while levels that can be tolerated are insufficient therapeutically. As a result, chemoresistance and subsequent tumor recurrence are often the outcome of such therapies. An example of this all too common event is the use of taxanes (paclitaxel and its semi-synthetic analogue, docetaxel) in the treatment of a variety of cancers including ovarian, breast, prostate, and non-small cell lung cancers. While surgery along with taxane- and platinum-based chemotherapy for advanced ovarian cancer has allowed up to 80% of women to achieve a clinical response, cancers in most patients initially diagnosed with late stage disease eventually recur.

Development of methods to circumvent resistance may ultimately improve the impact of adjuvant therapy, resulting in prolonged disease-free intervals and survival. Novel targeted therapies that interfere with specific molecular signaling pathways affecting cancer cell survival are being developed as potential treatment options to render cancer cells more sensitive to cytotoxic chemotherapy. Targeted therapies that increase cancer cell sensitivity to chemotherapies offer the benefits of lowering unwanted side effects and increasing the likelihood of destroying resistant cells while avoiding healthy cells where there is little or no expression of the targeted entity.

Recent studies have shown that sensitivity of ovarian cancer cells to the taxane, paclitaxel, is enhanced when the drug is administered in combination with an inhibitor of EGFR. EGFR and its ligand, epidermal growth factor (EGF), play critical roles in the progression of ovarian cancer through their effects on cellular proliferation, apoptosis, angiogenesis, and metastasis. EGFR is overexpressed or dysregulated in many solid tumors, and high levels are expressed in 33-98% of all epithelial ovarian cancers. Their high expression is believed to mitigate the effectiveness of taxane chemotherapy by inhibiting cell division and apoptosis. Reports of inhibition of EGFR with tyrosine kinase inhibitors (TKI) [e.g. gefitinib (Iressa)] and monoclonal antibodies (e.g. cetuximab) have demonstrated that silencing of receptor activity increases chemosensitization of tumor cells including ovarian cancer cells. While targeting EGFR as well as other members of the human EGFR (HER) family has proven successful, not all tumors that are expected to respond to these agents do so. Often, emergence of drug resistance occurs either by targeted mutation or induction of alternative signaling pathways. These results highlight the need for further targeted approaches.

Based on these findings, we sought to determine if siRNA against EGFR could be selectively delivered to ovarian cancer cells using a nanoparticle carrier. Targeted cancer therapy by RNA interference (RNAi) is a relatively new approach, and silencing EGFR by RNAi has already shown promising results. We report in the Example application of a novel and highly efficient method for the targeted delivery of EGFR siRNA to ovarian cancer cells. We used a 12 amino acid peptide (YSAYPDSVPMMS or "YSA") coupled to the surface of ~100-nm diameter core/shell nanogels [composed largely of poly(N-isopropylmethacrylamide) (pNIPMAm)] to permit cell-specific targeting, and the subsequent delivery of high concentrations of EGFR siRNA. The YSA peptide mimics the ligand ephrin-A1, which binds to the erythropoietin-producing hepatocellular (Eph) A2 receptor, while the core/shell nanogel offers an efficient vehicle for cell entry, and a protective environment for the siRNA, and a depot for its controlled release. Delivery of nanogel-loaded EGFR siRNA to EphA2 positive cells resulted in the loss of EGFR expression followed by a significant increase in the sensitivity of the targeted cells to docetaxel. Our results indicate that this approach may lead to considerable improvements in the treatment of ovarian and other cancers by increasing the efficacy of chemotherapy while simultaneously reducing the associated negative side effects.

Materials and Methods. All materials were purchased from Sigma-Aldrich (St Louis, Mo.) and used as received unless otherwise noted.

Nanogel synthesis. For the present Example, we utilized a nanogel structure that we have previously shown to have excellent siRNA encapsulation and release properties in the context of in vitro delivery. The synthesis of the nanogels has been described previously. Briefly, nanogel core particles were synthesized by free-radical precipitation polymerization using a molar composition of 98% N-isopropylmethacrylamide (NIPMAm), 2% N,N'-methylenebis(acrylamide) (BIS) and a small amount (~0.1 mM) acrylamidofluorescein (AFA) to render the nanogels fluorescent for visualization. The core nanogels were then used as seeds for the addition of a hydrogel shell [34, 35]. The shell composition was 97.5% NIPMAm, 2% BIS, and 0.5% aminopropylmethacrylamide (APMA, Polysciences, Warrington, Pa.). The APMA co-monomer was included to provide chemoligation sites for peptide immobilization.

Peptide conjugation. The YSA peptide (GenScript Corporation, Piscataway, N.J.) was conjugated to the nanogels via maleimide coupling to the cysteine residue on the C-terminal end of the peptides. Maleimide-functionalized nanogels were prepared via EDC coupling of ε-maleimidocaproic acid (EMCA) to the primary amines in the nanogel shell. Peptide coupling was performed by introducing the YSA peptide in a 1:1 molar ratio with amine (YSA molecular weight=1450.66 g/mol). The YSA peptide was then conjugated to the nanogels via maleimide coupling to the cysteine residue on the C-terminal end of the peptides.

Cell culture. Hey cells were provided by Gordon W Mills, Department of Systems Biology, the University of Texas, M. D. Anderson Cancer Center. Hey cells were cultured in RPMI 1640 (Mediatech, Manassas, Va.) supplemented with 10% v/v heat-inactivated fetal calf serum (Invitrogen, Carlsbad, Calif.), 2 mM L-glutamine (Mediatech), 10 mM HEPES buffer (Mediatech), penicillin (100 U/ml), and streptomycin (100 μg/mL). SK-OV-3 cells were purchased from the American Type Culture Collection (ATCC, Manassas, Va.) and were propagated in McCoy's 5A with L-glutamine (Mediatech) supplemented with 10% v/v heat-inactivated fetal calf serum (Atlanta Biologicals, Lawrenceville, Ga.), penicillin, and streptomycin (Mediatech).

RNA encapsulation. Hydrogels were loaded with siRNA as previously described in Example 1. Briefly, lyophilized nanogels were reswollen in the presence of the siRNA, thereby imbibing the solute within the hydrogel network. In a typical procedure, a 20 μM solution (250 μL) of EGFR siRNA (Dharmacon, Lafayette, Colo.) was prepared in phosphate buffered saline (PBS). Nanogels were resuspended in this mixture at a concentration of 4 mg per 250 μL of siRNA solution and allowed to shake overnight at room temperature. After the siRNA was encapsulated in the nanogels, they were centrifuged and resuspended to a final concentration of 10 mg/mL in cell culture medium or PBS. Based on this procedure, the final concentration of siRNA was determined to be 16.6 μg siRNA/mg of nanogels.

Immunoblotting. Hey or SK-OV-3 cells were plated into 6-well cell culture plates ($5 \times 10^5$ cells/well), and the cells allowed to adhere overnight at 37° C. in a 5% $CO_2$ atmosphere. After washing the wells with PBS and replacing the media, EGFR siRNA-loaded/YSA-conjugated nanogels were added to the wells. Cells were incubated for 4 hours, washed with PBS, and fresh medium was added to the cells. The cells were incubated at 37° C. and 5% $CO_2$ in wells for 24, 48, 72, 96, and 120 hours. Control wells were set up to include non-targeted/siRNA-encapsulated pNIPMAm particles, unloaded pNIPMAm particles, YSA alone, and untreated cells. Cells were lysed after the designated time points, and immunoblotting was carried out as described. To determine the optimal concentration of EGFR-siRNA needed for efficient reduction of EGFR expression, the nanogel loading procedure described above was used, but the concentration of particles delivered to each well was altered. The initial concentration of siRNA-encapsulated particles (1 mg/mL of nanogels/$5\times10^5$ cells) used for the time point experiments was added to the first well. The concentration of subsequent wells was reduced by 10 fold each, resulting in nanogel concentrations of 100, 10, and 1 ng/mL per $5\times10^5$ cells. After 4 hours of incubation with the nanogels, the cells were washed with PBS, and the medium was replaced. The cells were then incubated for an additional 48 hours, and the samples prepared for immunoblotting as described.

Treatment with docetaxel. Hey or SK-OV-3 cells were plated in 96-well cell culture plates at a concentration of $1\times10^4$ cells/well. Hey or SK-OV-3 cells were subjected to nanogel delivery of siRNA at nanogel concentrations of 1000, 100, 10, and 1 μg/mL. Forty-eight hours after siRNA delivery, docetaxel was added to Hey or SK-OV-3 cells at concentrations ranging from 0.01-1000 nM. Treatment wells were set up in triplicate, and the cells were incubated with docetaxel for an additional 4 days. After treatment, the cells were washed with PBS, and 100 μL of medium was added back to the wells. To this, 10 μL of Tox8 was added to determine cell viability. The cells were incubated with the Tox8 reagent according to the manufacturer's instructions. The fluorescence was measured ($\lambda_{em}$=560 nm, $\lambda_{ex}$=590 nm) by a Spectramax Gemini Fluorescence Microplate Reader (Molecular Devices, Sunnyvale, Calif.). Wells without cells but with Tox8 were used as controls and subtracted from all treatments as background. Each experiment was performed in duplicate.

Statistical analysis. Statistical analysis of the immunoblot data was performed using a non-parametric ANOVA (Kruskal Wallis) test. If significance was indicated, a Dunn's post-test was used to determine significance between groups. Statistical analysis of siRNA-loaded nanogels plus docetaxel treated Hey or SK-OV-3 cells was compared to all controls (pNIPMAm, YSA-pNIPMAm, YSA peptide alone, and untreated cells). To determine significance between groups, a one-way ANOVA test was performed. If significance was indicated, a Tukey post test was performed to determine significance between sample groups. In all cases, significance was defined as P<0.05.

Results. Down-regulation of EGFR in EphAr ovarian cancer (Hey) cells by targeted siRNA-loaded nanogels. By coupling a peptide-mimetic (YSAYPDSVPMMS) of the EphA2 receptor's ephrin-A1 ligand to core/shell hydrogel nanoparticles (nanogels), we demonstrated previously the ability to target the delivery of siRNA to ovarian cancer (Hey) cells expressing the EphA2 receptor. Importantly, these nanogels are nontoxic in both unmodified and targeted forms, and enabled the delivery of siRNA in serum-containing media. To further establish the efficacy and specificity of this targeting method, we established a model using ovarian cancer cell lines either positive or negative for expression of EphA2 and positive for expression of EGFR. FIG. 9A contrasts the high level of EphA2 receptor expression by Hey cells with the lack of EphA2 expression in the SK-OV-3 cancer cell line. Detection of EGFR was noted in both cell lines by immunoblotting (FIG. 9B). Because of the observed differences in EphA2 expression levels, we hypothesized that the level of EGFR siRNA delivery and the subsequent decrease in EGFR expression in the cell lines would depend upon the presence of the EphA2 receptor as well as the concentration of siRNA loaded-nanogels added to the cells. Based upon this premise, reduction of EGFR expression in SK-OV-3 cells (EphA2 negative) should not be observed.

To test this hypothesis and measure the efficacy of the siRNA loaded nanogels in our system, we determined the time course of EGFR knockdown using EphA2 positive Hey cells. Lyophilized YSA-targeted nanogels were loaded with of EGFR siRNA by reswelling the particles in a concentrated solution of siRNA, as described. This method results in high efficiency siRNA encapsulation (93±1%) and approximately 70% retention of the siRNA after the first 12 hours. Long retention times may provide slow and continuous release of siRNA leading to prolonged reduction of the expressed target. Following siRNA encapsulation, the loaded nanogels were added to Hey cells and incubated at 37° C. for four hours. In all experiments, we maintained a constant nanogel/cell ratio of 1 mg/mL of nanogels/$5\times10^5$ cells, unless noted. Unincorporated nanogels were removed by washing and subsequent replacement of the cell culture medium. Treated cells were incubated for an additional 24, 48, 72, 96, and 120 hours to determine the time course of EGFR reduction by the nanogel-delivered siRNA. At each time point, the cells were lysed and the samples were prepared for immunoblotting to determine the EGFR levels. FIG. 10A shows the average percent decrease in EGFR expression at each time point. A significant decrease in EGFR expression (*P<0.01) was observed at both 48 and 72 hours when compared to untreated (UT) controls. Significance (^P<0.05) was also observed at the 96 hour time point when compared to untreated cells. These results indicate a maximum reduction of EGFR expression at 48 hours, and reexpression of EGFR beginning at approximately 72 hours. Expression gradually increased through 120 hours but did not return to pretreatment levels. This may be due to the slow but continuous release of siRNA from the nanogels. A slight decrease in EGFR expression was noted in the unloaded, YSA-targeted nanogel control, which may be due to cross-talk between the EGFR and the EphA2 receptors. In addition, a small decrease in EGFR expression was observed when cells were incubated with nanogels alone, but these decreases were not significant (P>0.05). A representative immunoblot is shown in FIG. 10B.

To determine the dose response for the delivery vector, EGFR siRNA-loaded nanogels were incubated with Hey cells using 10-fold serial dilutions of siRNA-loaded nanogels so that the nanogel concentration ranged from 1 μg/mL to 1 mg/mL per $5\times10^5$ cells. Cells were harvested 48 hours after nanogel addition, and the cell lysates were analyzed by immunoblotting. Decreased levels of EGFR were observed at all concentrations (FIG. 11A). A significant decrease (*P<0.01) in EGFR expression was observed at the highest dose of delivered nanogels (1 mg/mL) when compared to YSA-targeted/unloaded nanogels, and complete reduction of EGFR expression was observed with as little as 10 μg/mL of siRNA-loaded nanogels. An immunoblot of a representative experiment is shown in FIG. 11B.

The role of the peptide-targeted receptor, EphA2, in nanogel uptake, and the level of nonspecific nanogel incorporation into cells were explored through the use of an EphA2 negative cell line, SK-OV-3. Because these cells lack EphA2 expression, we hypothesized that the YSA-targeted nanogels would not be taken up by SK-OV-3 cells through receptor-mediated endocytosis of EphA2. Consequently, EGFR expression should not differ between targeted/siRNA-loaded nanogels and controls. Any particle uptake could then be designated as nonspecific. For these studies, siRNA (1 mg/mL of nanogels) was loaded into YSA-pNIPMAm nanogels and added to $5 \times 10^5$ SK-OV-3 cells. Ten-fold serial dilutions of the nanogels were carried to assess the affects of nanogel concentration on the levels of EGFR. After 48 hours, harvested samples were examined for receptor expression by immunoblotting. As expected, expression of EGFR was not decreased after treatment with the loaded nanogels regardless of the concentration of nanogels used (FIG. 12). Expression levels in SK-OV-3 cells treated with siRNA-loaded nanogels did not differ from controls demonstrating the high specificity of the targeted nanogels for EphA2 positive cells but not for EphA2 negative cells.

Epidermal growth factor receptor down-regulation in siRNA-loaded nanogel treated cells sensitizes ovarian cancer cells to docetaxel. Expression of EGFR is significantly related to chemosensitivity in many cancers. The concept of chemosensitization by EGFR blockade was provided by studies utilizing EGFR-blocking antibodies in combination with cisplatin or doxorubicin in human tumor xenografts. Studies using a tyrosine kinase inhibitor against EGFR showed an increased sensitivity of ovarian cancer cell lines to paclitaxel after preincubation with the inhibitor. To determine if our targeted delivery of EGFR siRNA to ovarian cancer cells could be used to increase cell line sensitivity to taxanes, Hey cells were incubated with EGFR siRNA-loaded nanogel for 48 hours to allow for maximum reduction in EGFR expression (see FIGS. 10A and B). After 48 hours, cells were treated with increasing concentrations of docetaxel (0.1 to 1000 nM), and the percent cytotoxicity was assessed. The results presented (FIG. 12A) demonstrate the docetaxel sensitivity of treated Hey cells was almost 8-fold greater than untreated controls. While Hey cells treated with nanogel controls also showed increased chemosensitivity (FIG. 12B), these changes were significantly less than those observed in cells treated with the YSA-targeted, siRNA-loaded nanogels ($P<0.01$). Exceptions included the pNIPMAM and YSA-pNIPMAm controls where docetaxel concentrations were 0-0.1 ($P>0.05$) at all nanogel concentrations examined, and for pNIPMAm and YSA-pNIPMAm controls when 1 ng/ml siRNA-loaded nanogels were delivered to cells followed by incubation with 1 nM docetaxel ($P>0.05$). Because SK-OV-3 cells lack expression of EphA2, and thereby lack the means for receptor-mediated endocytosis of the targeted nanogels, we did not expect the sensitivity of SK-OV-3 cells to docetaxel to be altered. Whereas an increase in cytotoxicity of the siRNA-loaded nanogel treated SK-OV-3 cells was noted as the concentration of docetaxel was increased, unlike the effect observed in the Hey cell line, sensitivity to the drug did not differ significantly from controls ($P>0.05$) (FIGS. 14A and B). These results corroborate our earlier findings that EGFR levels are not decreased in this cell line after treatment with siRNA-loaded nanogels. It also substantiates the high specificity of our peptide-targeted system, and demonstrates little or no nonspecific uptake of nanogels by SK-OV-3 cells as shown by the constant levels of EGFR expression and unaltered chemosensitivity after nanogel treatment.

Conclusion. Novel therapies that interfere with specific molecular signaling pathways have potential as treatment options since they render cancer cells more sensitive to cytotoxic therapy. Although the role of EGFR in altering tumor chemosensitivity has not yet been fully elucidated, preclinical studies have suggested that blockade of EGFR, and the resulting reversal of chemoresistance in many tumor types is a viable strategy for treatment of cancers where frontline therapies have failed to induce a cure. Chemosensitization by EGFR inhibition was demonstrated in early studies using blocking antibodies in combination with cisplatin or doxorubicin in human tumor xenografts. This same effect was later observed using small TKIs such as gefitinib (Iressa). Silencing of EGFR by RNAi is an alternative to anti-EGFR therapy, and this approach has already shown promising results.

While Example 1 demonstrated the specificity of YSA-targeted siRNA-loaded nanogels to cells expressing EphA2, the studies presented in Example 2 serve as further validation of EphA2 as a target for translatable therapeutic strategies. The EphA2 receptor is overexpressed in a variety of cancers including ~75% of ovarian malignancies, and expression of the receptor is associated with poor prognosis, increased metastasis, and decreased survival. EphA2 shows limited expression in adults, with expression restricted to a few epithelial tissues. Thus, due to its expression pattern, localization, and functional importance in treatment outcome, EphA2 is an attractive target for therapeutic agents in ovarian as well as other cancers. Several approaches have been used to target EphA2 for cancer therapy either by taking advantage of the tumor-promoting function of EphA2 to modulate cell behavior and suppress tumor growth, or using EphA2 as a means to deliver agents, such as exogenous drugs, to tumor cells and the tumor microenvironment.

In this Example, we noticed that treatment of Hey cells with the YSA peptide showed diminished EGFR expression when compared to untreated controls (FIGS. 10A and B). Furthermore, Hey cells treated with the YSA peptide alone also showed an increased sensitivity to docetaxel when compared to untreated controls (FIG. 13B). These differences were significant ($P<0.05$) at docetaxel doses of 1 nM and higher. Our results indicate that activation of EphA2 by the YSA peptide and subsequent EphA2 degradation may lead to a reduction in EGFR expression indicating cross-talk between the two receptor signaling pathways. In fact, two recent studies have shown that EphA2 interacts with members of the EGFR receptor family, and these interactions may be important for targeted therapies involving EphA2 and EGFR. Mice harboring ErbB2 (a member of the EGFR family) in mammary epithelium were sensitive to inhibition of EphA2 when compared to controls without ErbB2. EphA2 formed a complex with ErbB2 in both human and murine breast carcinoma cells, leading to enhanced signaling through Ras-MAPK activation and ultimately promoting tumor progression. In addition, activated EGFR and the constitutively active EGFR type III deletion mutant (EGFRvIII) were shown to induce the expression of EphA2 in mammalian cell lines. Loss of EphA2 expression reduced cell motility of EGFR-overexpressing cell lines. Thus, the interaction of EphA2 with members of the EGFR family indicates a functional role for EphA2 in EGFR-expressing cancer cells. In our system, loss or reduction of EphA2 through interaction with YSA-functionalized nanogels may provide an enhanced effect over delivery of EGFR siRNA alone leading to a dual-targeting strategy for chemosensitzation of ovarian tumors.

The ability of siRNAs to potently but reversibly silence genes in vivo has made them particularly well suited as a drug therapeutic. However, poor stability under physiological conditions limits the utility of systemic delivery of siRNA, and its high molecular weight (~13 kDa) and polyanionic nature prevent transport across the cell membrane, further compounding the problem of therapeutic application. Thus, delivery represents the main hurdle for broader development of siRNA therapeutics. To our knowledge, the work presented here along with our previous studies, provides the first description using targeted, poly(alkylacrylamide)-based nanogels for siRNA delivery. Furthermore, the core/shell nanogel delivery system employed here is readily amendable to selective surface functionalization by a variety of targeting molecules, offers a protective environment for sensitive cargo, and shows excellent targeting uptake and delivery in serum containing medium. The nanogel particles are also exceedingly simple to load, and extremely high (>90%) degrees of siRNA incorporation are observed. These properties and the low toxicity levels indicated thus far by this formulation along with the low immunotoxcity demonstrated recently by Li et al [28] indicate the promise of overcoming some of the final obstacles hindering siRNA driven therapeutic strategies. Future studies investigating the in vivo delivery of siRNAs to tumors using nanogels, and the effect on chemosensitization will aid in the refinement of targeted siRNA delivery for treatment of ovarian cancer.

SEQUENCES

SEQ ID NO 1
Tyr-Ser-Ala-Tyr-Pro-Asp-Ser-Val-Pro-Met-Met-Ser-Cys

SEQ ID NO 2
Asp-Tyr-Pro-Ser-Met-Ala-Met-Tyr-Ser-Pro-Ser-Val-Cys

What is claimed is:

1. A nanogel-based delivery system comprising: a nanogel comprising a crosslinked polymer particle and a crosslinked polymer shell, disposed substantially around the crosslinked polymer particle; and an active agent contained substantially within the nanogel, wherein the active agent is non-covalently associated with the nanogel; wherein the crosslinked polymer particle comprises poly(N-isopropylmethacrylamide) and N,N'-methylenebis(acrylamide), and the crosslinked polymer shell comprises a functionalization agent.

2. The nanogel-based delivery system of claim 1, wherein the crosslinked polymer shell comprises poly(N-isopropylmethacrylamide), N,N'-methylenebis(acrylamide), and aminopropylmethacryamide.

3. The nanogel-based delivery system of claim 2, wherein the active agent is a small interfering ribonucleic acid (siRNA).

4. The nanogel-based delivery system of claim 3, wherein the siRNA comprises substantial sequence identity to a target gene expressed in a neoplastic disease.

5. The nanogel-based delivery system of claim 1, wherein the nanogel further comprises a targeting moiety, wherein the targeting moiety is attached to the crosslinked polymer shell through the functionalization agent, and wherein the targeting moiety is displayed on at least a portion of the crosslinked polymer shell.

6. The nanogel-based delivery system of claim 5, wherein the targeting moiety comprises a peptide having the amino acid sequence YSAYPDSVPMMSC (SEQ ID NO: 1).

7. The nanogel-based delivery system of claim 6, wherein the active agent comprises a siRNA having substantial sequence identity to a gene encoding epidermal growth factor receptor.

8. A method of delivering an active agent into a cell, the method comprising:
    contacting a nanogel with a cell, the nanogel comprising
        a crosslinked polymer particle wherein the crosslinked polymer particle comprises poly(N-isopropylmethacrylamide) and N,N'-methylenebis(acrylamide),
        a crosslinked polymer shell disposed substantially around the crosslinked polymer particle and comprising a functionalization agent, and
        the active agent contained substantially within the nanogel, wherein the active agent is non-covalently associated with the nanogel; and
    delivering the active agent to the cell.

9. The method of claim 8, wherein the active agent comprises a siRNA.

10. The method of claim 9, wherein the nanogel further comprises a targeting moiety and the crosslinked polymer shell comprises poly(N-isopropylmethacrylamide), N,N'-methylenebis(acrylamide), and aminopropylmethacryamide, wherein the targeting moiety is attached to the crosslinked polymer shell through the functionalization agent, and wherein the targeting moiety is displayed on at least a portion of the crosslinked polymer shell.

11. The method of claim 10, further comprising reducing expression of a target gene, wherein the siRNA has substantial sequence identity to the target gene.

12. The method of claim 11, wherein the target gene encodes one or more of an anti-apoptotic molecule, a growth factor, a growth factor receptor, a mitotic spindle protein, a cell cycle protein, an angiogenic factor, an oncogene, an intracellular signal transducer, or a molecular chaperone.

13. The method of claim 12, wherein the targeting moiety comprises a peptide having the amino acid sequence YSAYPDSVPMMSC (SEQ ID NO: 1), and wherein the active agent is a siRNA having substantial sequence identity to the target gene, the target gene encoding epidermal growth factor receptor.

14. A method for treating neoplastic disease comprising:
administering to a subject having neoplastic disease an effective amount of a nanogel comprising
a crosslinked polymer particle;
a crosslinked polymer shell comprising a functionalization agent, wherein the crosslinked polymer shell is disposed substantially around the crosslinked polymer particle;
a targeting moiety comprising a peptide having the amino acid sequence YSAYPDSVPMMSC (SEQ ID NO: 1), wherein the targeting moiety is attached to the crosslinked polymer shell through the functionalization agent, and wherein the targeting moiety is displayed on at least a portion of the crosslinked polymer shell; and
an active agent contained substantially within the nanogel, wherein the active agent is non-covalently associated with the nanogel;
wherein the neoplastic disease comprises cells expressing the EphA2 receptor.

15. The method of treating neoplastic disease of claim 14, wherein the crosslinked polymer particle comprises poly(N-isopropylmethacrylamide) and N,N'-methylenebis (acrylamide), and wherein the crosslinked polymer shell comprises poly(N-isopropylmethacrylamide), N,N'-methylenebis (acrylamide), and aminopropylmethacryamide.

16. The method of treating neoplastic disease of claim 15, further comprising reducing expression of a target gene, wherein the active agent is a siRNA, the siRNA having substantial sequence identity to the target gene, and wherein the target gene encodes one or more of an anti-apoptotic molecule, a growth factor, a growth factor receptor, a mitotic spindle protein, a cell cycle protein, an angiogenic factor, an oncogene, an intracellular signal transducer, or a molecular chaperone.

17. The method of treating neoplastic disease of claim 16, wherein the target gene encodes epidermal growth factor receptor.

18. The method of treating neoplastic disease of claim 17, further comprising increasing sensitivity of the subject to a chemotherapeutic agent.

19. The method of treating neoplastic disease of claim 18, wherein the chemotherapeutic agent comprises paclitaxel or docetaxel.

* * * * *

SEQUENCE LISTING

```
<160> NUMBER OF SEQ ID NOS: 2

<210> SEQ ID NO 1
<211> LENGTH: 13
<212> TYPE: PRT
<213> ORGANISM: Homo sapiens

<400> SEQUENCE: 1

Tyr Ser Ala Tyr Pro Asp Ser Val Pro Met Met Ser Cys
1               5                   10

<210> SEQ ID NO 2
<211> LENGTH: 13
<212> TYPE: PRT
<213> ORGANISM: Artificial Sequence
<220> FEATURE:
<223> OTHER INFORMATION: SCRAMBLED FORM OF SEQ ID NO 1

<400> SEQUENCE: 2

Asp Tyr Pro Ser Met Ala Met Tyr Ser Pro Ser Val Cys
1               5                   10
```